(12) United States Patent
Uhlmann et al.

(10) Patent No.: US 7,615,539 B2
(45) Date of Patent: Nov. 10, 2009

(54) NUCLEIC ACID-LIPOPHILIC CONJUGATES

(75) Inventors: Eugen Uhlmann, Glashuetten (DE); Jörg Vollmer, Duesseldorf (DE); Arthur M. Krieg, Wellesley, MA (US)

(73) Assignees: Coley Pharmaceutical Group, Inc., New York, NY (US); Coley Pharmaceutical GmbH, Dusseldorf (DE)

( * ) Notice: Subject to any disclaimer, the term of this patent is extended or adjusted under 35 U.S.C. 154(b) by 430 days.

(21) Appl. No.: 10/952,254

(22) Filed: Sep. 27, 2004

(65) Prior Publication Data

US 2005/0130911 A1 Jun. 16, 2005

Related U.S. Application Data

(60) Provisional application No. 60/505,977, filed on Sep. 25, 2003.

(51) Int. Cl.
| | |
|---|---|
| *A01N 25/26* | (2006.01) |
| *A01N 25/28* | (2006.01) |
| *A01N 43/04* | (2006.01) |
| *A61F 13/00* | (2006.01) |
| *C07H 21/00* | (2006.01) |
| *C07H 21/04* | (2006.01) |
| *C07H 21/02* | (2006.01) |
| *A61K 9/127* | (2006.01) |
| *A61K 9/52* | (2006.01) |
| *A61K 9/16* | (2006.01) |
| *A61K 9/50* | (2006.01) |
| *A61K 31/70* | (2006.01) |

(52) U.S. Cl. ............. 514/44; 514/45; 514/49; 536/23.1; 536/25.3; 536/25.6; 424/420; 424/417; 424/418; 424/419; 424/434; 424/450; 424/457; 424/490; 424/491

(58) Field of Classification Search ............ None
See application file for complete search history.

(56) References Cited

U.S. PATENT DOCUMENTS

| | | | |
|---|---|---|---|
| 5,416,203 A | 5/1995 | Letsinger | |
| 5,527,899 A | 6/1996 | Froehler | |
| 5,646,126 A | 7/1997 | Cheng et al. | |
| 5,663,153 A | 9/1997 | Hutcherson et al. | |
| 5,723,335 A | 3/1998 | Hutcherson et al. | |
| 5,780,448 A | 7/1998 | Davis | |
| 5,929,226 A | 7/1999 | Padmapriya et al. | |
| 5,948,611 A * | 9/1999 | Prockop et al. .............. 435/6 |
| 5,968,909 A | 10/1999 | Agrawal et al. | |
| 6,030,955 A | 2/2000 | Stein et al. | |
| 6,031,086 A | 2/2000 | Switzer | |
| 6,121,434 A | 9/2000 | Peyman et al. | |
| 6,194,388 B1 | 2/2001 | Krieg et al. | |
| 6,207,646 B1 | 3/2001 | Krieg et al. | |
| 6,207,819 B1 | 3/2001 | Manoharan et al. | |
| 6,214,806 B1 | 4/2001 | Krieg et al. | |
| 6,218,371 B1 | 4/2001 | Krieg et al. | |
| 6,221,882 B1 | 4/2001 | Macfarlane | |
| 6,239,116 B1 | 5/2001 | Krieg et al. | |
| 6,339,068 B1 | 1/2002 | Krieg et al. | |
| 6,348,312 B1 | 2/2002 | Peyman et al. | |
| 6,399,630 B1 | 6/2002 | Macfarlane | |
| 6,406,705 B1 | 6/2002 | Davis et al. | |
| 6,429,199 B1 | 8/2002 | Krieg et al. | |
| 6,476,000 B1 | 11/2002 | Agrawal et al. | |
| 6,479,504 B1 | 11/2002 | Macfarlane et al. | |
| 6,521,637 B2 | 2/2003 | Macfarlane | |
| 6,562,798 B1 | 5/2003 | Schwartz | |
| 6,589,940 B1 | 7/2003 | Raz et al. | |
| 6,605,708 B1 | 8/2003 | Habus et al. | |
| 6,610,308 B1 | 8/2003 | Haensler | |
| 6,610,661 B1 | 8/2003 | Carson et al. | |
| 6,653,292 B1 | 11/2003 | Krieg et al. | |
| 6,692,917 B2 * | 2/2004 | Neri et al. .................. 435/6 |
| 6,727,230 B1 | 4/2004 | Hutcherson et al. | |
| 6,815,429 B2 | 11/2004 | Agrawal | |
| 6,821,957 B2 | 11/2004 | Krieg et al. | |
| 6,822,086 B1 * | 11/2004 | Papisov .................. 536/24.2 |
| 6,835,395 B1 | 12/2004 | Semple et al. | |
| 6,943,240 B2 | 9/2005 | Bauer et al. | |
| 6,949,520 B1 | 9/2005 | Hartmann et al. | |
| 7,001,890 B1 * | 2/2006 | Wagner et al. ............. 514/44 |
| 7,105,495 B2 | 9/2006 | Agrawal et al. | |
| 7,223,741 B2 * | 5/2007 | Krieg ..................... 514/44 |
| 7,229,974 B2 * | 6/2007 | Peyman et al. ............. 514/44 |
| 7,271,156 B2 * | 9/2007 | Krieg et al. .............. 514/44 |
| 7,276,489 B2 * | 10/2007 | Agrawal et al. ........... 514/44 |
| 7,402,572 B2 * | 7/2008 | Krieg et al. .............. 514/44 |

(Continued)

FOREIGN PATENT DOCUMENTS

EP 0 092 574 A1 4/1983

(Continued)

OTHER PUBLICATIONS

Joseph et al, Vaccine, 2002, 20:3342-3354.*

(Continued)

*Primary Examiner*—N. M Minnifield
(74) *Attorney, Agent, or Firm*—Wolf, Greenfield & Sacks, P.C.; Gregg C. Benson

(57) ABSTRACT

The invention relates to a nucleic acid-lipophilic conjugates and methods for modulating an immune response using the conjugates. The lipophilic moiety associated with an immunostimulatory nucleic acid.

27 Claims, 8 Drawing Sheets

U.S. PATENT DOCUMENTS

| | | | |
|---|---|---|---|
| 7,407,944 B2 * | 8/2008 | Agrawal et al. | 514/44 |
| 7,517,861 B2 * | 4/2009 | Krieg et al. | 514/44 |
| 7,524,828 B2 * | 4/2009 | Krieg et al. | 514/44 |
| 2001/0044416 A1 | 11/2001 | McCluskie et al. | |
| 2002/0064515 A1 | 5/2002 | Krieg et al. | |
| 2002/0091097 A1 | 7/2002 | Bratzler et al. | |
| 2002/0137714 A1 | 9/2002 | Kandimalla et al. | |
| 2002/0156033 A1 | 10/2002 | Bratzler et al. | |
| 2002/0164341 A1 | 11/2002 | Davis et al. | |
| 2002/0165178 A1 | 11/2002 | Schetter et al. | |
| 2002/0198165 A1 | 12/2002 | Bratzler et al. | |
| 2003/0026782 A1 | 2/2003 | Krieg et al. | |
| 2003/0026801 A1 | 2/2003 | Weiner et al. | |
| 2003/0050230 A1 * | 3/2003 | Plowman et al. | 514/12 |
| 2003/0050261 A1 | 3/2003 | Krieg et al. | |
| 2003/0050263 A1 | 3/2003 | Krieg et al. | |
| 2003/0050268 A1 | 3/2003 | Krieg et al. | |
| 2003/0055014 A1 | 3/2003 | Bratzler | |
| 2003/0086900 A1 | 5/2003 | Low et al. | |
| 2003/0087848 A1 | 5/2003 | Bratzler et al. | |
| 2003/0091599 A1 | 5/2003 | Davis et al. | |
| 2003/0100527 A1 | 5/2003 | Krieg et al. | |
| 2003/0104523 A1 | 6/2003 | Bauer et al. | |
| 2003/0118635 A1 | 6/2003 | Dalsgaard et al. | |
| 2003/0119773 A1 | 6/2003 | Raz et al. | |
| 2003/0125279 A1 | 7/2003 | Junghans et al. | |
| 2003/0139364 A1 | 7/2003 | Krieg et al. | |
| 2003/0148316 A1 | 8/2003 | Lipford et al. | |
| 2003/0148976 A1 | 8/2003 | Krieg et al. | |
| 2003/0166001 A1 | 9/2003 | Lipford | |
| 2003/0175731 A1 | 9/2003 | Fearon et al. | |
| 2003/0181406 A1 | 9/2003 | Schetter et al. | |
| 2003/0186912 A1 | 10/2003 | Agrawal | |
| 2003/0191079 A1 | 10/2003 | Krieg et al. | |
| 2003/0199466 A1 | 10/2003 | Fearon et al. | |
| 2003/0212026 A1 | 11/2003 | Krieg et al. | |
| 2003/0224010 A1 | 12/2003 | Davis et al. | |
| 2003/0232074 A1 | 12/2003 | Lipford et al. | |
| 2003/0232856 A1 | 12/2003 | Macfarlane | |
| 2004/0006034 A1 | 1/2004 | Raz et al. | |
| 2004/0009949 A1 | 1/2004 | Krieg | |
| 2004/0030118 A1 | 2/2004 | Wagner et al. | |
| 2004/0038922 A1 | 2/2004 | Haensler et al. | |
| 2004/0047869 A1 | 3/2004 | Garcon et al. | |
| 2004/0053880 A1 | 3/2004 | Krieg | |
| 2004/0058883 A1 | 3/2004 | Phillips et al. | |
| 2004/0067902 A9 | 4/2004 | Bratzler et al. | |
| 2004/0067905 A1 | 4/2004 | Krieg | |
| 2004/0087534 A1 | 5/2004 | Krieg et al. | |
| 2004/0087538 A1 | 5/2004 | Krieg et al. | |
| 2004/0092472 A1 | 5/2004 | Krieg | |
| 2004/0097719 A1 | 5/2004 | Agrawal et al. | |
| 2004/0106568 A1 | 6/2004 | Krieg et al. | |
| 2004/0131628 A1 | 7/2004 | Bratzler et al. | |
| 2004/0132677 A1 | 7/2004 | Fearon et al. | |
| 2004/0132685 A1 | 7/2004 | Krieg et al. | |
| 2004/0136948 A1 | 7/2004 | Fearon et al. | |
| 2004/0142469 A1 | 7/2004 | Krieg et al. | |
| 2004/0143112 A1 | 7/2004 | Krieg et al. | |
| 2004/0147468 A1 | 7/2004 | Krieg et al. | |
| 2004/0152649 A1 | 8/2004 | Krieg | |
| 2004/0152656 A1 | 8/2004 | Krieg et al. | |
| 2004/0152657 A1 | 8/2004 | Krieg et al. | |
| 2004/0162258 A1 | 8/2004 | Krieg et al. | |
| 2004/0162262 A1 | 8/2004 | Krieg et al. | |
| 2004/0167089 A1 | 8/2004 | Krieg et al. | |
| 2004/0171150 A1 | 9/2004 | Krieg et al. | |
| 2004/0171571 A1 | 9/2004 | Krieg et al. | |
| 2004/0181045 A1 | 9/2004 | Krieg et al. | |
| 2004/0198680 A1 | 10/2004 | Krieg | |
| 2004/0198688 A1 | 10/2004 | Krieg et al. | |
| 2004/0224323 A1 * | 11/2004 | Plowman et al. | 435/6 |
| 2004/0229835 A1 | 11/2004 | Krieg et al. | |
| 2004/0234512 A1 | 11/2004 | Wagner et al. | |
| 2004/0235770 A1 * | 11/2004 | Davis et al. | 514/44 |
| 2004/0235774 A1 | 11/2004 | Bratzler et al. | |
| 2004/0235777 A1 | 11/2004 | Wagner et al. | |
| 2004/0235778 A1 | 11/2004 | Wagner et al. | |
| 2004/0259153 A1 * | 12/2004 | Kurosawa et al. | 435/7.1 |
| 2004/0266719 A1 | 12/2004 | McCluskie et al. | |
| 2005/0004061 A1 | 1/2005 | Krieg et al. | |
| 2005/0004062 A1 | 1/2005 | Krieg et al. | |
| 2005/0009774 A1 | 1/2005 | Krieg et al. | |
| 2005/0032734 A1 | 2/2005 | Krieg et al. | |
| 2005/0032736 A1 | 2/2005 | Krieg et al. | |
| 2005/0037403 A1 | 2/2005 | Krieg et al. | |
| 2005/0037985 A1 | 2/2005 | Krieg et al. | |
| 2005/0043529 A1 | 2/2005 | Davis et al. | |
| 2005/0049215 A1 | 3/2005 | Krieg et al. | |
| 2005/0049216 A1 | 3/2005 | Krieg et al. | |
| 2005/0054601 A1 | 3/2005 | Wagner et al. | |
| 2005/0054602 A1 | 3/2005 | Krieg et al. | |
| 2005/0059619 A1 | 3/2005 | Krieg et al. | |
| 2005/0059625 A1 | 3/2005 | Krieg et al. | |
| 2005/0070491 A1 | 3/2005 | Krieg et al. | |
| 2005/0075302 A1 | 4/2005 | Hutcherson et al. | |
| 2005/0100983 A1 | 5/2005 | Bauer et al. | |
| 2005/0101554 A1 | 5/2005 | Krieg et al. | |
| 2005/0101557 A1 | 5/2005 | Krieg et al. | |
| 2005/0119273 A1 | 6/2005 | Lipford et al. | |
| 2005/0123523 A1 | 6/2005 | Krieg et al. | |
| 2005/0130911 A1 | 6/2005 | Uhlmann et al. | |
| 2005/0130918 A1 | 6/2005 | Agrawal et al. | |
| 2005/0148537 A1 | 7/2005 | Krieg et al. | |
| 2005/0169888 A1 | 8/2005 | Hartman et al. | |
| 2005/0171047 A1 | 8/2005 | Krieg et al. | |
| 2005/0181422 A1 | 8/2005 | Bauer et al. | |
| 2005/0182017 A1 | 8/2005 | Krieg | |
| 2005/0197314 A1 | 9/2005 | Krieg et al. | |
| 2005/0215500 A1 | 9/2005 | Krieg et al. | |
| 2005/0215501 A1 | 9/2005 | Lipford et al. | |
| 2006/0014713 A1 | 1/2006 | Agrawal et al. | |
| 2006/0019909 A1 | 1/2006 | Agrawal et al. | |
| 2006/0074040 A1 | 4/2006 | Kandimalla et al. | |
| 2006/0140875 A1 * | 6/2006 | Krieg et al. | 424/46 |
| 2006/0189550 A1 | 8/2006 | Jiang et al. | |
| 2006/0211641 A1 | 9/2006 | Agrawal et al. | |
| 2006/0287261 A1 | 12/2006 | Agrawal et al. | |
| 2006/0287262 A1 | 12/2006 | Agrawal et al. | |
| 2008/0045473 A1 * | 2/2008 | Uhlmann et al. | 514/44 |

FOREIGN PATENT DOCUMENTS

| | | |
|---|---|---|
| EP | 0 302 758 A1 | 2/1989 |
| EP | 0 468 520 A2 | 1/1992 |
| EP | 1595946 * | 11/2005 |
| WO | WO 85/00261 * | 1/1985 |
| WO | WO 96/02555 A1 | 2/1996 |
| WO | WO 98/11211 A2 | 3/1998 |
| WO | WO 98/49288 A1 | 11/1998 |
| WO | WO 98/55495 A2 | 12/1998 |
| WO | WO 99/56755 A1 | 11/1999 |
| WO | WO 99/58118 A2 | 11/1999 |
| WO | WO 99/62923 A2 | 12/1999 |
| WO | WO 00/06588 A1 | 2/2000 |
| WO | WO 00/15256 A2 | 3/2000 |
| WO | WO 00/54803 A2 | 9/2000 |
| WO | WO 01/12804 A2 | 2/2001 |
| WO | WO 01/22972 A2 | 4/2001 |
| WO | WO 01/85751 A1 | 11/2001 |
| WO | WO 02/26757 A2 | 4/2002 |
| WO | WO 03/035836 A2 | 5/2003 |
| WO | WO 03/040308 A2 * | 5/2003 |
| WO | WO 03/066649 A1 | 8/2003 |

| | | | |
|---|---|---|---|
| WO | WO 03/094963 A2 | | 11/2003 |
| WO | WO 2004/007743 A2 | | 1/2004 |
| WO | WO 2004/087203 | * | 10/2004 |
| WO | WO 2004/094671 A2 | | 11/2004 |
| WO | WO 2005/030259 A1 | * | 4/2005 |
| WO | WO 2006/056142 A1 | * | 6/2006 |
| WO | WO 2006/079291 A1 | * | 8/2006 |
| WO | WO 2006/108358 A1 | * | 10/2006 |

OTHER PUBLICATIONS

Singh et al, International Journal for Parasitology, 2003, 33:469-478.*
Tafaghodi et al, European J. Pharmaceutics and Biopharmaceutics, 2006, 64:138-145.*
Vollmer, International Reviews Immunology, Aug. 2006, 25/3-4:125-134 abstract only.*
Kuramoto et al, J. Controlled Release, 2006, 115:226-233.*
Mitchell et al, Vaccine, 2006, 24:5300-5310.*
Ludewig et al, Vaccine, 2001, 19:23-32.*
Gursel et al, Vaccine, 1999, 17:1376-1383.*
Li et al, Vaccine, 2002, 20:148-157.*
O'Hagan et al, Biomolecular Engineering, 2001, 18:69-85.*
Cooke et al, Tetrahedron Letters, 2006, 47:719-722.*
Agarwal et al, Trends in Mol. Med., 2002, 8:114-121.*
Weiner, J. Leukocyte Biology, 2000, 68:456-463.*
Agarwal et al, Molecular Med. Today, 2000, 6:72-81.*
Kuramoto et al, J. Controlled Release, 2008, 126:274-280.*
Letsinger, R.L., et al., Cholesteryl-conjugated oligonucleotides: synthesis, properties, and activity as inhibitors of replication of human immunodeficiency virus in cell culture. *Proc Natl Acad Sci U S A.* Sep. 1989;86(17):6553-6.
Letsinger, R.L., et al., Synthesis and properties of modified oligonucleotides, *Nucleic Acids Symp Ser.* 1991;(24):75-8.
MacKellar, C., et al., Synthesis and physical properties of anti-HIV antisense oligonucleotides bearing terminal lipophilic groups. *Nucleic Acids Res.* Jul. 11, 1992;20(13):3411-7.
Polanczyk, M., Immunostimulatory effects of DNA and CpG motifs. *Centr Eur J Immunol.* 2000;25(3):160-6.
Aggrawal et al., Pharmacokinetics, biodistribution, and stability of oligodeoxynucleotide phosphorothioates in mice. Proc Natl Acad Sci U S A. Sep. 1, 1991;88(17):7595-9.
Askew et al., CpG DNA induces maturation of dendritic cells with distinct effects on nascent and recycling MHC-II antigen-processing mechanisms. J Immunol. Dec. 15, 2000 ;165(12):6889-95.
Ballas et al., Induction of NK activity in murine and human cells by CpG motifs in oligodeoxynucleotides and bacterial DNA. J Immunol. Sep. 1, 1996 ;157(5):1840-5.
Bauer et al., DNA activates human immune cells through a CpG sequence-dependent manner. Immunology. Aug. 1999;97(4):699-705.
Boggs et al., Characterization and modulation of immune stimulation by modified oligonucleotides. Antisense Nucleic Acid Drug Dev. Oct. 1997 ;7(5):461-71.
Broide et al., DNA-Based immunization for asthma. Int Arch Allergy Immunol. Feb.-Apr. 1999;118(2-4):453-6.
Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;165(11):6278-86.
Chace et al., Bacterial DNA-induced NK cell IFN-gamma production is dependent on macrophage secretion of IL-12. Clin Immunol Inununopathol. Aug. 1997;84(2):185-93.
Choi et al., The level of protection against rotavirus shedding in mice following immunization with a chimeric VP6 protein is dependent on the route and the coadministered adjuvant. Vaccine. Mar. 15, 2002 ;20(13-14):1733-40.
Chu et al., CpG oligodeoxynucleotides act as adjuvants that switch on T helper 1 (Th1) immunity. J Exp Med. Nov. 17, 1997;186(10):1623-31.
Cohen, Selective anti-gene therapy for cancer: principles and prospects. Tohoku J Exp Med. Oct. 1992;168(2):351-9.

Cowdery et al., Bacterial DNA induces NK cells to produce IFN-gamma in vivo and increases the toxicity of lipopolysaccharides. J Immunol. Jun. 15, 1996;156(12):4570-5.
Davis, Use of CpG DNA for enhancing specific immune responses. Curr Top Microbiol Immunol. 2000;247:171-83.
Garegg et al., Nucleoside H-phosphonates. IV. Automated solid phase synthesis of oligoribonucleotides by the hydrogenphosphonate approach. Tetrahedron Lett. 1986; 27(34):4055-8.
Goodman et al., Selective modulation of elements of the immune system by low molecular weight nucleosides. J Pharmacol Exp Ther. Sep. 1995;274(3):1552-7.
Gouttefangeas et al., Problem solving for tumor immunotherapy. Nat Biotechnol. May 2000;18(5):491-2.
Hadden et al., lmmunostimulants. Trends Pharmacol Sci. May 1993;14(5):169-74.
Hahm et al., Efficacy of polyadenylic.polyuridylic acid in the treatment of chronic active hepatitis B. Int J Immunopharmacol. Mar. 1994;16(3):217-25.
Halpern et al., Bacterial DNA induces murine interferon-gamma production by stimulation of interleukin-12 and tumor necrosis factor-alpha. Cell Immunol. Jan. 10, 1996;167(1):72-8.
Harrington et al., Adjuvant effects of low doses of a nuclease-resistant derivative of polyinosinic acid. polycytidylic acid on antibody responses of monkeys to inactivated Venezuelan equine encephalomyelitis virus vaccine. Infect Immun. Apr. 1979;24(1):160-6.
Hartmann et al., CpG DNA and LPS induce distinct patterns of activation in human monocytes. Gene Ther. May 1999;6(5):893-903.
Hartmann et al., Mechanism and function of a newly identified CpG DNA motif in human primary B cells. J Immunol. Jan. 15, 2000;164(2):944-53.
Hartmann et al., Delineation of a CpG phosphorothioate oligodeoxynucleotide for activating primate immune responses in vitro and in vivo. J Immunol. Feb. 1, 2000;164(3):1617-24.
Hartmann et al., CpG DNA: a potent signal for growth, activation, and maturation of human dendritic cells. Proc Natl Acad Sci U S A. Aug. 3, 1999;96(16):9305-10.
Heeg et al., CpG DNA as a Th1 trigger. Int Arch Allergy Immunol. Feb. 2000;121(2):87-97.
Henry et al., Chemically modified oligonucleotides exhibit decreased immune stimulation in mice. J Pharmacol Exp Ther. Feb. 2000;292(2):468-79.
Hopkin et al., BioMedNet, Issue 57, Jun. 25, 1999.
Huang et al., Induction and regulation of Th1-inducing cytokines by bacterial DNA, lipopolysaccharide, and heat-inactivated bacteria. Infect Immun. Dec. 1999;67(12):6257-63.
Iho et al., Oligodeoxynucleotides containing palindrome sequences with internal 5'-CpG-3' act directly on human NK and activated T cells to induce IFN-gamma production in vitro. J Immunol. Oct. 1, 1999;163(7):3642-52.
Iversen et al., In vivo studies with phosphorothioate oligonucleotides: pharmacokinetics prologue. Anticancer Drug Des. Dec. 1991;6(6):531-8.
Jakob et al., Activation of cutaneous dendritic cells by CpG-containing oligodeoxynucleotides: a role for dendritic cells in the augmentation of Th1 responses by immunostimulatory DNA. J Immunol. Sep 15, 1998;161(6):3042-9.
Jakob et al., Bacterial DNA and CpG-containing oligodeoxynucleotides activate cutaneous dendritic cells and induce IL-12 production: implications for the augmentation of Th1 responses. Int Arch Allergy lmmunol. Feb.-Apr. 1999;118(2-4):457-61.
Jiang et al., Enhancing immunogenicity by CpG DNA. Curr Opin Mol Ther. Apr. 2003;5(2):180-5.
Juffermans et al., CpG oligodeoxynucleotides enhance host defense during murine tuberculosis. Infect Immun. Jan. 2002;70(1):147-52.
Kandimalla et al., A dinucleotide motif in oligonucleotides shows potent immunomodulatory activity and overrides species-specific recognition observed with CpG motif. Proc Natl Acad Sci U S A. Nov. 25, 2003;100(24):14303-8. Epub Nov 10, 2003.
Kandimalla et al., Towards optimal design of second-generation immunomodulatory oligonucleotides. Curr Opin Mol Ther. Apr. 2002;4(2):122-9.

Kandimalla et al., Divergent synthetic nucleotide motif recognition pattern: design and development of potent immunomodulatory oligodeoxyribonucleotide agents with distinct cytokine induction profiles. Nucleic Acids Res. May 1, 2003;31(9):2393-400.

Kataoka et al., Antitumor activity of synthetic oligonucleotides with sequences from cDNA encoding proteins of Mycobacterium bovis BCG. Jpn J Cancer Res. Mar. 1992;83(3):244-7.

Kataoka et al., Immunotherapeutic potential in guinea-pig tumor model of deoxyribonucleic acid from Mycobacterium bovis BCG complexed with poly-L-lysine and carboxymethylcellulose. Jpn J Med Sci Biol. Oct. 1990;43(5):171-82.

Kimura et al., Binding of oligoguanylate to scavenger receptors is required for oligonucleotides to augment NK cell activity and induce IFN. J Biochem (Tokyo). Nov. 1994;116(5):991-4.

Klinman et al., Immunotherapeutic applications of CpG-containing oligodeoxynucleotides. Drug News Perspect. Jun. 2000; 13(5):289-96.

Klinman et al., Immune recognition of foreign DNA: a cure for bioterrorism? Immunity. Aug. 1999;11(2):123-9.

Klinman et al., Contribution of CpG motifs to the immunogenicity of DNA vaccines. J Immunol. Apr. 15, 1997;158(8):3635-9.

Klinman et al., CpG motifs present in bacteria DNA rapidly induce lymphocytes to secrete interleukin 6, interleukin 12, and interferon gamma. Proc Natl Acad Sci U S A. Apr. 2, 1996;93(7):2879-83.

Kovarik et al., CpG oligodeoxynucleotides can circumvent the Th2 polarization of neonatal responses to vaccines but may fail to fully redirect Th2 responses established by neonatal priming. J Immunol. Feb. 1, 1999;162(3):1611-7.

Kranzer et al. CpG-oligodeoxynucleotides enhance T-cell receptor-triggered interferon-gamma production and up-regulation of CD69 via induction of antigen-presenting cell-derived interferon type I and interleukin-12. Immunology. Feb. 2000;99(2):170-8.

Krieg et al., Immune effects and therapeutic applications of CpG motifs in bacterial DNA. Immunopharmacology. Jul. 25, 2000;48(3):303-5.

Krieg et al., American College of Rheumatology 58th National Scientific Meeting. Minneapolis, Minnesota, Oct. 22, 1994. Abstracts. Arthritis Rheum. Sep. 1994;37(9 Suppl).

Krieg et al., Oligodeoxynucleotide modifications determine the magnitude of B cell stimulation by CpG motifs. Antisense Nucleic Acid Drug Dev. 1996 Summer;6(2):133-9.

Krieg et al., Phosphorothioate oligodeoxynucleotides: antisense or anti-protein? Antisense Res Dev. 1995 Winter;5(4):241.

Krieg et al., Applied Antisense Oligonucleotide Technology, 431-448, 1998.

Krieg, CpG DNA: a pathogenic factor in systemic lupus erythematosus? J Clin Immunol. Nov. 1995;15(6):284-92.

Krieg et al., CpG motifs in bacterial DNA trigger direct B-cell activation. Nature. Apr. 6, 1995;374(6522):546-9.

Krieg et al., The role of CpG dinucleotides in DNA vaccines. Trends Microbiol. Jan. 1998;6(1):23-7.

Krieg, An innate immune defense mechanism based on the recognition of CpG motifs in microbial DNA. J Lab Clin Med. Aug. 1996;128(2):128-33.

Krieg et al., CpG motifs in bacterial DNA and their immune effects. Annu Rev Immunol. 2002;20:709-60. Epub Oct. 4, 2001.

Krieg et al., Causing a commotion in the blood: immunotherapy progresses from bacteria to bacterial DNA. Immunol Today. Oct. 21, 2000(10):521-6.

Krieg et al., Chapter 8: Immune Stimulation by Oligonucleotides. in Antisense Research and Application. Crooke, editor. 1998; 243-62.

Krieg et al., P-chirality-dependent immune activation by phosphorothioate CpG oligodeoxynucleotides. Oligonucleotides. 2003;13(6):491-9.

Krieg et al., 1996 Meeting on Molecular Approaches to the Control of Infectious Diseases. Cold Spring Harbor Laboratory, Sep. 9-13, 1996: p. 116.

Krieg et al., Enhancing vaccines with immune stimulatory CpG DNA. Cur Opin Mol Ther. Feb. 2001;3(1):15-24.

Krieg et al., Ernst Schering Research Found Workshop, (30): 105-18, 2001.

Krieg, Immune effects and mechanisms of action of CpG motifs. Vaccine. Nov. 8, 2000;19(6):618-22.

Krieg et al., Immune stimulation by oligonucleotides. In Antisense Research and Application. S. T. Crooke, editor. Springer, Heidelberg. 1998: 471-515.

Krieg et al., Mechanisms and applications of immune stimulatory CpG oligodeoxynucleotides. Biochim Biophys Acta. Dec. 10, 1999;1489(1):107-16.

Krieg et al., The CpG motif: Implications for clinical immunology. BioDrugs. Nov. 1, 1998;10(5):341-6.

Krieg, The role of CpG motifs in innate immunity. Curr Opin Immunol. Feb. 2000;12(1):35-43.

Krieg et al., Mechanism of action of CpG DNA. Curr Top Microbiol Immunol. 2000;247:1-21.

Krieg et al., Mechanisms and therapeutic applications of immune stimulatory CpG DNA. Pharmacol Ther. Nov. 1999;84(2):113-20.

Krieg et al., Sequence motifs in adenoviral DNA block immune activation by stimulatory CpG motifs. Proc Natl Acad Sci U S A. Oct. 13, 1998;95(21):12631-6.

Krieg et al., CpG DNA induces sustained IL-12 expression in vivo and resistance to Listeria monocytogenes challenge. J Immunol. Sep. 1, 1998;161(5):2428-34.

Krieg, Signal transduction induced by immunostimulatory CpG DNA. Springer Semin Immunopathol. 2000;22(1-2):97-105.

Krieg, Lymphocyte activation by CpG dinucleotide motifs in prokaryotic DNA. Trends Microbiol. Feb. 1996;4(2):73-6.

Kuramoto et al., Changes of host cell infiltration into Meth A fibrosarcoma tumor during the course of regression induced by injections of a BCG nucleic acid fraction. Int J Immunopharmacol. Jul. 1992;14(5):773-82.

Kuramoto et al., Oligonucleotide sequences required for natural killer cell activation. Jpn J Cancer Res. Nov. 1992;83(11):1128-31.

Kuramoto et al., In situ infiltration of natural killer-like cells induced by intradermal injection of the nucleic acid fraction from BCG. Microbiol Immunol. 1989;33(11):929-40.

Lipford et al., CpG-containing synthetic oligonucleotides promote B and cytotoxic T cell responses to protein antigen: a new class of vaccine adjuvants. Eur J Immunol. Sep. 1997;27(9):2340-4.

Lipford et al., Immunostimulatory DNA: sequence-dependent production of potentially harmful or useful cytokines. Eur J Immunol. Dec. 1997;27(12):3420-6.

Lipford et al., Bacterial DNA as immune cell activator. Trends Microbiol. Dec. 1998;6(12):496-500.

Martin-Orozco et al., Enhancement of antigen-presenting cell surface molecules involved in cognate interactions by immunostimulatory DNA sequences. Int Immunol. Jul. 1999;11(7):1111-8.

McCluskie et al., CpG DNA is a potent enhancer of systemic and mucosal immune responses against hepatitis B surface antigen with intranasal administration to mice. J Immunol. Nov. 1, 1998;161(9):4463-6.

McCluskie et al., CpG DNA as mucosal adjuvant. Vaccine, 18: 231-237, 2000.

McCluskie et al., Oral, intrarectal and intranasal immunizations using CpG and non-CpG oligodeoxynucleotides as adjuvants. Vaccine. Oct. 15, 2000;19(4-5):413-22.

McCluskie et al., CpG DNA is an effective oral adjuvant to protein antigens in mice. Vaccine. Nov. 22, 2000;19(7-8):950-7.

McCluskie et al., The use of CpG DNA as a mucosal vaccine adjuvant. Curr Opin Investig Drugs. Jan. 2001;2(1):35-9.

McCluskie et al., The role of CpG in DNA vaccines. Springer Semin Immunopathol. 2000;22(1-2):125-32.

Mojcik et al., Administration of a phosphorothioate oligonucleotide antisense to murine endogenous retroviral MCF env causes immune effects in vivo in a sequence-specific manner. Clin Immunol Immunopathol. May 1993;67(2):130-6.

Nielson et al., Peptide nucleic acid (PNA). A DNA mimic with a peptide backbone. Bioconjug Chem. Jan.-Feb. 1994;5(1):3-7.

Payette et al., History of vaccines and positioning of current trends. Curr Drug Targets Infect Disord. Nov. 2001; 1(3):241-7.

Pisetsky et al., The immunologic properties of DNA. J Immunol. Jan. 15, 1996;156(2):421-3.

Pisetsky et al., Influence of backbone chemistry on immune activation by synthetic oligonucleotides. Biochem Pharmacol. Dec. 15, 1999;58(12):1981-8.

Pisetsky, Immunologic consequences of nucleic acid therapy. Antisense Res Dev. 1995 Fall;5(3):219-25.

Pisetsky et al., Stimulation of in vitro proliferation of murine lymphocytes by synthetic oligodeoxynucleotides. Mol Biol Rep. Oct. 1993;18(3):217-21.

Pisetsky, The influence of base sequence on the immunostimulatory properties of DNA. Immunol Res. 1999;19(1):35-46.

Rankin et al., CpG motif identification for veterinary and laboratory species demonstrates that sequence recognition is highly conserved. Antisense Nucleic Acid Drug Dev. Oct. 2001;11(5):333-40.

Ray et al., Experimental Biology 2001. Orlando, Florida, USA. Mar. 31-Apr. 4, 2001. Abstracts, part II. FASEB J. Mar. 8, 2001;15(5):A1007.

Reitz et al., Small-molecule immunostimulants. Synthesis and activity of 7,8-disubstituted guanosines and structurally related compounds. J Med Chem. Oct. 14, 1994;37(21):3561-78.

Rodgers et al., Effects of acute administration of O,S,S-trimethyl phosphorodithioate on the generation of cellular and humoral immune responses following in vitro stimulation. Toxicology. Oct. 1988;51(2-3):241-53.

Roman et al., Immunostimulatory DNA sequences function as T helper-1-promoting adjuvants. Nat Med. Aug. 1997;3(8):849-54.

Rothenfusser et al., Recent advances in immunostimulatory CpG oligonucleotides. Curr Opin Mol Ther. Apr. 2003;5(2):98-106.

Sato et al., Immunostimulatory DNA sequences necessary for effective intradermal gene immunization. Science. Jul 19, 1996;273(5273):352-4.

Schwartz et al., Bacterial DNA or oligonucleotides containing unmethylated CpG motifs can minimize lipopolysaccharide-induced inflammation in the lower respiratory tract through an IL-12-dependent pathway. J Immunol. Jul. 1, 1999;163(1):224-31.

Sester et al., Phosphorothioate backbone modification modulates macrophage activation by CpG DNA. J Immunol. Oct. 15, 2000;165(8):4165-73.

Sparwasser et al., Bacterial DNA causes septic shock. Nature. Mar. 27, 1997;386(6623):336-7.

Sparwasser et al., Macrophages sense pathogens via DNA motifs: induction of tumor necrosis factor-alpha-mediated shock. Eur J Immunol. Jul. 1997;27(7):1671-9.

Stein et al., Problems in interpretation of data derived from in vitro and in vivo use of antisense oligodeoxynucleotides. Antisense Res Dev. 1994 Summer;4(2):67-9.

Stein et al., Physicochemical properties of phosphorothioate oligodeoxynucleotides. Nucleic Acids Res. Apr. 25, 1988;16(8):3209-21.

Stirchak et al., Uncharged stereoregular nucleic acid analogs: 2. Morpholino nucleoside oligomers with carbamate internucleoside linkages. Nucleic Acids Res. Aug. 11, 1989;17(15):6129-41.

Stunz et al., Inhibitory oligonucleotides specifically block effects of stimulatory CpG oligonucleotides in B cells. Eur J Immunol. May 2002;32(5):1212-22.

Sun et al. Type I interferon-mediated stimulation of T cells by CpG DNA. J Exp Med. Dec. 21, 1998;188(12):2335-42.

Sun et al. Multiple effects of immunostimulatory DNA on T cells and the role of type I interferons. Springer Semin Immunopathol. 2000;22(1-2):77-84.

Tarköy et al., Nucleic-Acid Analogues with Constraint Conformational Flexibility in the Sugar-Phosphate Backbone ('Bicyclo-DNA'). Part 1. Preparation of (3S,5'R)-2'-Deoxy-3',5'-ethano-αβ-D-ribonucleosides ('Bicyclonucleosides'). Helv Chim Acta. Feb. 10, 1993;76(1): 481-510.

Threadgill et al., Mitogenic synthetic polynucleotides suppress the antibody response to a bacterial polysaccharide. Vaccine. Jan. 1998;16(1):76-82.

Tokunaga et al., A synthetic single-stranded DNA, poly(dG,dC), induces interferon-alpha/beta and- gamma, augments natural killer activity, and suppresses tumor growth. Jpn J Cancer Res. Jun. 1988;79(6):682-6.

Tokunaga et al., Synthetic oligonucleotides with particular base sequences from the cDNA encoding proteins of Mycobacterium bovis BCG induce interferons and activate natural killer cells. Microbiol Immunol. 1992;36(1):55-66.

Tortora at al., Oral antisense that targets protein kinase A cooperates with taxol and inhibits tumor growth, aniogenesis, and growth factor production. Clin Cancer Res. Jun. 2000;6(6):2506-12.

Uhlmann et al., Recent advances in the development of immunostimulatory oligonucleotides. Curr Opin Drug Discov Devel. Mar. 2003;6(2):204-17.

Vanenddriessche et al., Acyclic oligonucleotides: possibilities and limitations. Tetrahedron. Aug. 13, 1993;49(33): 7223-38.

Vollmer et al., Highly immunostimulatory CpG-free oligodeoxynucleotides for activation of human leukocytes. Antisense Nucleic Acid Drug Dev. Jun. 2002;12(3):165-75.

Vollmer et al., Characterization of three CpG oligodeoxynucleotide classes with distinct immunostimulatory activities. Eur J Immunol. Jan. 2004;34(1):251-62.

Vollmer et al., Modulation of CpG oligodeoxynucleotide-mediated immune stimulation by locked nucleic acid (LNA). Oligonucleotides. 2004 Spring;14(1):23-31.

Wagner, Interactions between bacterial CpG-DNA and TLR9 bridge innate and adaptive immunity. Curr Opin Microbiol. Feb. 2002;5(1):62-9.

Weeratna et al., CpG ODN can re-direct the Th bias of established Th2 immune responses in adult and young mice. FEMS Immunol Med Microbiol. Dec. 2001;32(1):65-71.

Weeratna et al., CpG DNA induces stronger immune responses with less toxicity than other adjuvants. Vaccine. Mar. 6, 2000;18(17):1755-62.

Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.

Wernette et al., CpG oligodeoxynucleotides stimulate canine and feline immune cell proliferation. Vet Immunol Immunopathol. Jan. 15, 2002;84(3-4):223-36.

Wyatt et al. Combinatorially selected guanosine-quartet structure is a potent inhibitor of human immunodeficiency virus envelope-mediated cell fusion. Proc Natl Acad Sci U S A. Feb. 15, 1994;91(4):1356-60.

Yamamoto et al., Lipofection of synthetic oligodeoxyribonucleotide having a palindromic sequence of AACGTT to murine splenocytes enhances interferon production and natural killer activity. Microbiol Immunol. 1994;38(10):831-6.

Yamamoto et al., Unique palindromic sequences in synthetic oligonucleotides are required to induce IFN [correction of INF] and augment IFN-mediated [correction of INF] natural killer activity. J Immunol. Jun. 15, 1992;148(12):4072-6.

Yamamoto et al., [Commemorative lecture of receiving Imamura Memorial Prize. II. Mode of action of oligonucleotide fraction extracted from Mycobacterium bovis BCG]Kekkaku. Sep. 1994;69(9):571-4. Japanese.

Yamamoto et al., Ability of oligonucleotides with certain palindromes to induce interferon production and augment natural killer cell activity is associated with their base length. Antisense Res Dev. 1994 Summer;4(2):119-22.

Yamamoto et al., Synthetic oligonucleotides with certain palindromes stimulate interferon production of human peripheral blood lymphocytes in vitro. Jpn J Cancer Res. Aug. 1994;85(8):775-9.

Yi et al. Rapid induction of mitogen-activated protein kinases by immune stimulatory CpG DNA. J Immunol. Nov. 1, 1998;161(9):4493-7.

Yi et al., Rapid immune activation by CpG motifs in bacterial DNA. Systemic induction of IL-6 transcription through an antioxidant-sensitive pathway. J Immunol. Dec. 15, 1996 ;157(12):5394-402.

Yi et al., IFN-gamma promotes IL-6 and IgM secretion in response to CpG motifs in bacterial DNA and oligodeoxynucleotides. J Immunol. Jan. 15, 1996;156(2):558-64.

Yi et al. CpG oligodeoxyribonucleotides rescue mature spleen B cells from spontaneous apoptosis and promote cell cycle entry. J Immunol. Jun. 15, 1998;160(12):5898-906.

Zhao et al., Pattern and kinetics of cytokine production following administration of phosphorothioate oligonucleotides in mice. Antisense Nucleic Acid Drug Dev. Oct. 1997;7(5):495-502.

Zhao et al., Effect of different chemically modified oligodeoxynucleotides on immune stimulation. Biochem Pharmacol. Jan. 26, 1996;51(2):173-82.

Agrawal et al., Pharmacokinetics of oligonucleotides. Ciba Found Symp. 1997;209:60-75; discussion 75-8.

Agrawal et al., Absorption, tissue distribution and in vivo stability in rats of a hybrid antisense oligonucleotide following oral administration. Biochem Pharmacol. Aug. 8, 1995;50(4):571-6.

Agrawal et al., Pharmacokinetics of antisense oligonucleotides. Clin Pharmacokinet. Jan. 1995;28(1):7-16.

Agrawal et al., Chapter 19: Pharmacokinetics and bioavailability of antisense oligonucleotides following oral and colorectal administrations in experimental animals. 1998: 525-43.

Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.

Coley Pharmaceutical Group, Press Release, Jan. 22, 2007, Coley Pharmaceutical Group Updates Hepatitis C Drug Development Strategy.

Coley Pharmaceutical Group, Press Release, Jun. 20, 2007, Coley Pharmaceutical Group Announces Pfizer's Discontinuation of Clinical Trials for PF-3512676 Combined with Cytotoxic Chemotherapy in Advanced Non Small Cell Lung Cancer.

Crooke et al., Phosphorothioate Oligonucleotides. Therapeut Apps. 1995;ch5:63-84.

Dalpke et al., CpG-DNA as immune response modifier. Int J Med Microbiol. Oct. 2004;294(5):345-54.

Hafner et al., Antimetastatic effect of CpG DNA mediated by type I IFN. Cancer Res. Jul. 15, 2001;61(14):5523-8.

Hudson et al., Nucleic acid dendrimers: Novel biopolymer structures. J Am Chem Soc. 1993;115:2119-24.

Hybridon, Press Release, Hybridon Shows Immunomodulatory Activity of Synthetic Oligonucleotides, May 7, 2001.

Jäschke et al., Automated incorporation of polyethylane glycol into synthetic oligonucleotides. Tetrahedron Lett. 1993;34(2):301-4.

Kandimalla et al., Effect of chemical modifications of cytosine and guanine in a CpG-motif of oligonucleotides: structure-immunostimulatory activity relationships. Bioorg Med Chem. Mar. 2001;9(3):807-13.

Klinman et al., Immunotherapeutic uses of CpG oligodeoxynucleotides. Nat Rev Immunol. Apr. 2004;4(4):249-58.

Krieg et al., CpG DNA: a novel immunomodulator. Trends Microbiol. Feb. 1999;7(2):64-5.

Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004;27(6):460-71.

Kuramoto et al., Induction of T-cell-mediated immunity against MethA fibrosarcoma by intratumoral injections of a bacillus Calmette-Guerin nucleic acid fraction. Cancer Immunol Immunother. 1992;34(5):283-8.

Messina et al., The influence of DNA structure on the in vitro stimulation of murine lymphocytes by natural and synthetic polynucleotide antigens. Cell Immunol. Mar. 1993;147(1):148-57.

Mutwiri et al., Strategies for enhancing the immunostimulatory effects of CpG oligodeoxynucleotides. J Control Release. May 31, 2004;97(1):1-17.

Pisetsky et al., The influence of base sequence on the immunological properties of defined oligonucleotides. Immunopharmacology. Nov. 1998;40(3):199-208.

Rudginsky et al., Antitumor activity of cationic lipid complexed with immunostimulatory DNA. Mol Ther. Oct. 2001;4(4):347-55.

Satoh et al., The study of mechanisms in CpG oligodeoxynucleotides-induced aggravation in murine allergic contact dermititis to 2,4-dinitrofluorobenzene. Fulcushima Igaku Zasshi. 2002;52(3):237-50.

Sonehara et al., Hexamer palindromic oligonucleotides with 5'-CG-3' motif(s) induce production of interferon. J Interferon Cytokine Res. Oct. 1996;16(10):799-803.

Stein et al., Non-antisense effects of oligodeoxynucleotides. Antisense Technology. 1997; ch11: 241-64.

Tam et al., Liposomal encapsulation enhances the activity of immunostimulatory oligonucleotides. Future Lipidology. Feb. 2006; 1(1): 35-46.

Whitmore et al., Systemic administration of LPD prepared with CpG oligonucleotides inhibits the growth of established pulmonary metastases by stimulating innate and acquired antitumor immune responses. Canc Immun Immunother. 2001;50:503-14.

Yu et al., Accessible 5'-end of CpG-containing phosphorothioate oligodeoxynucleotides is essential for immunostimulatory activity. Bioorg Med Chem Lett. Dec. 4, 2000;10(23):2585-8.

Yu et al., Modulation of immunostimulatory activity of CpG oligonucleotides by site-specific deletion of nucleobases. Bioorg Med Chem Lett. Sep. 3, 2001;11(17):2263-7.

Zhao et al., Site of chemical modifications in CpG containing phosphorothioate oligodeoxynucleotide modulates its immunostimulatory activity. Bioorg Med Chem Lett. Dec. 20, 1999;9(24):3453-8. Abstract only.

Zhao et al., Immunostimulatory activity of CpG containing phosphorothioate oligodeoxynucleotide is modulated by modification of a single deoxynucleoside. Bioorg Med Chem Lett. May 15, 2000;10(10):1051-4. Abstract Only.

Zhu et al., Modulation of ovalbumin-induced Th2 responses by second-generation immunomodulatory oligonucleotides in mice. Int Immunopharmacol. Jul. 2004;4(7):851-62.

King et al., eds., A Dictionary of Genetics, Fifth Edition, Oxford University Press, 1997:246.

* cited by examiner

Figure 1: Lipophilic conjugates demonstrate enhanced IFN-α production.
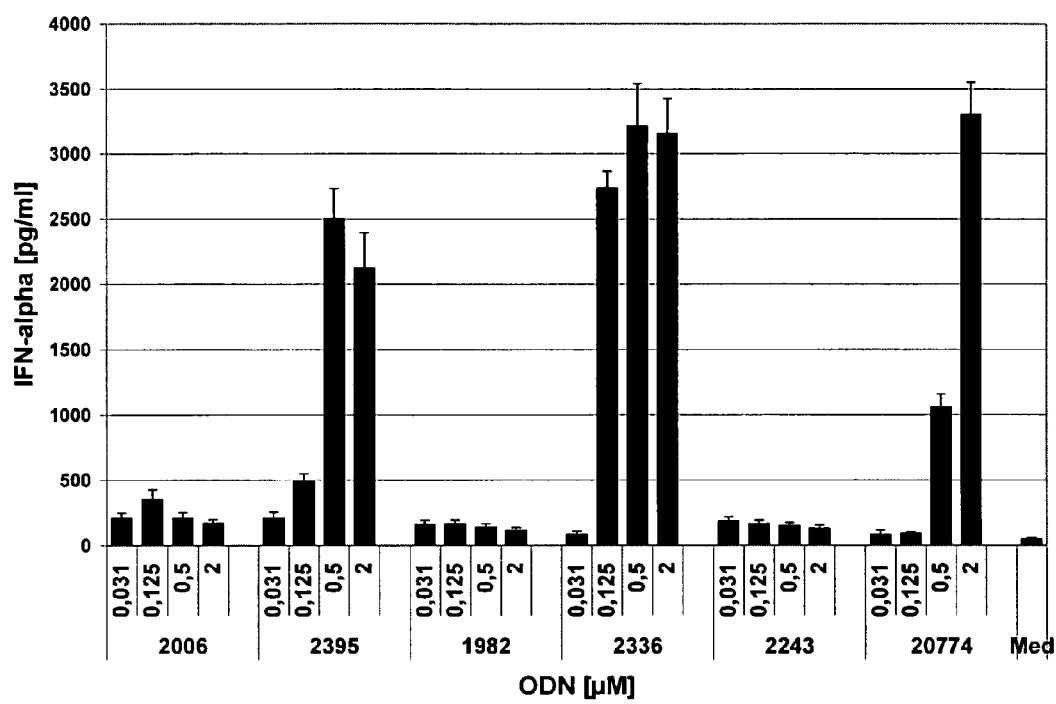

Figure 2: Lipophilic conjugates induce IL-6 secretion from human PBMC.
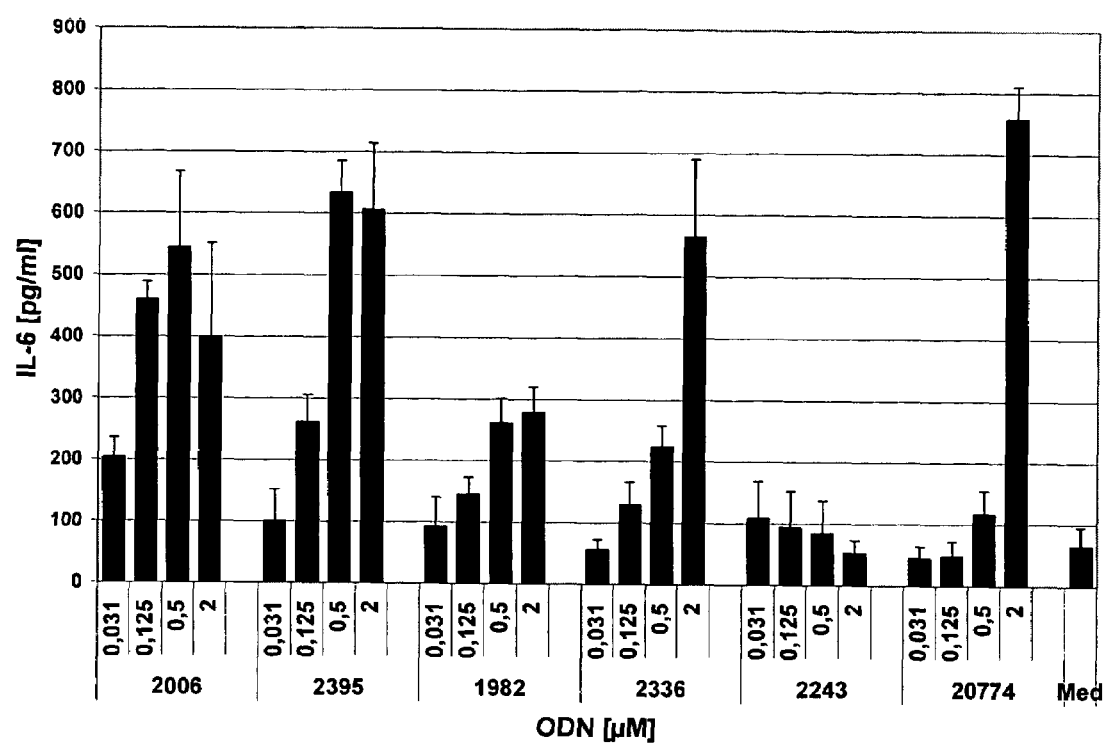

Figure 3: Lipophilic conjugates induce IL-10 secretion from human PBMC with reduced potency and efficacy.
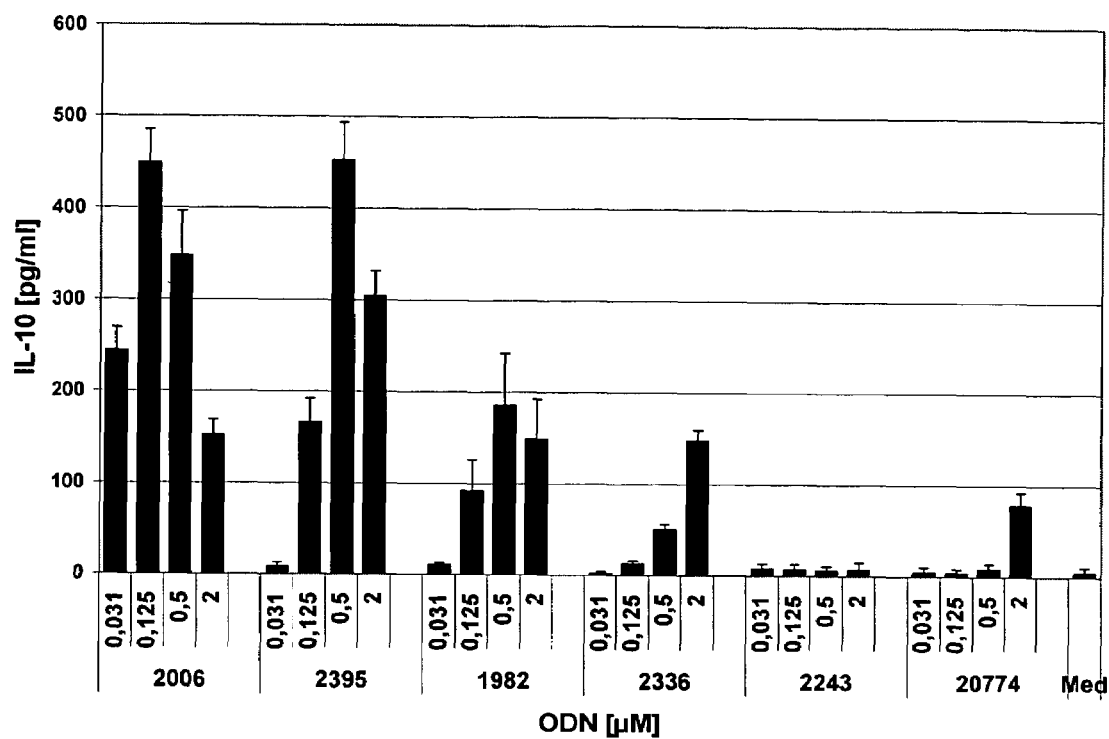

Figure 4: Lipophilic conjugates induce TLR9-dependent NFκB signalling.
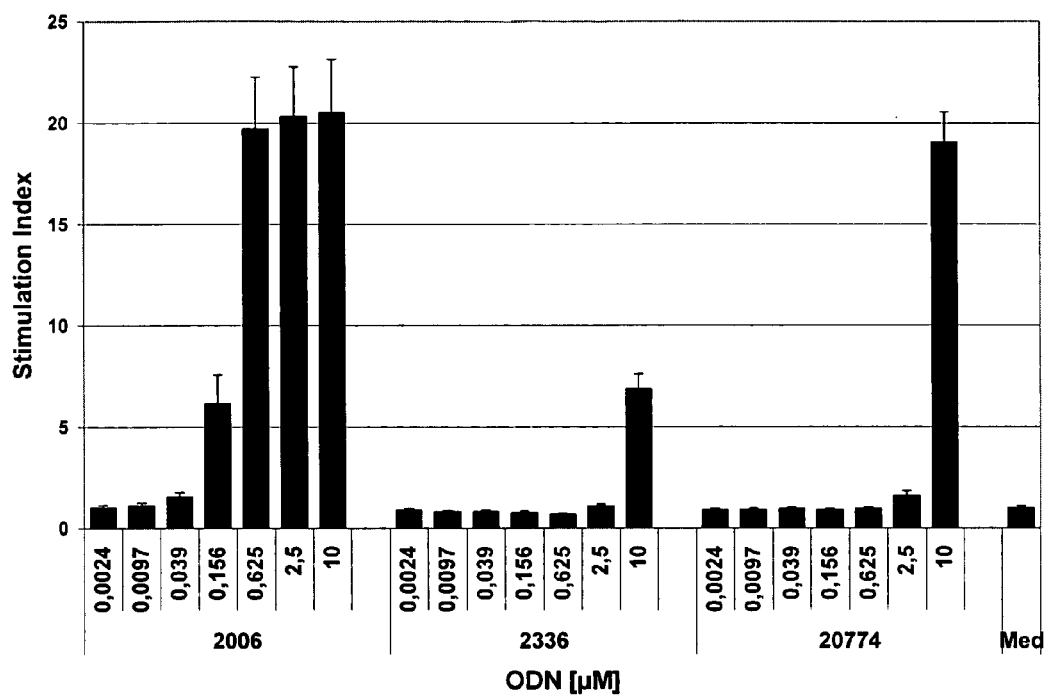

Figure 5: Lipophilic conjugates demonstrate *in vitro* mouse splenocyte stimulation of IL-12, IL-6 and TNF-α production.
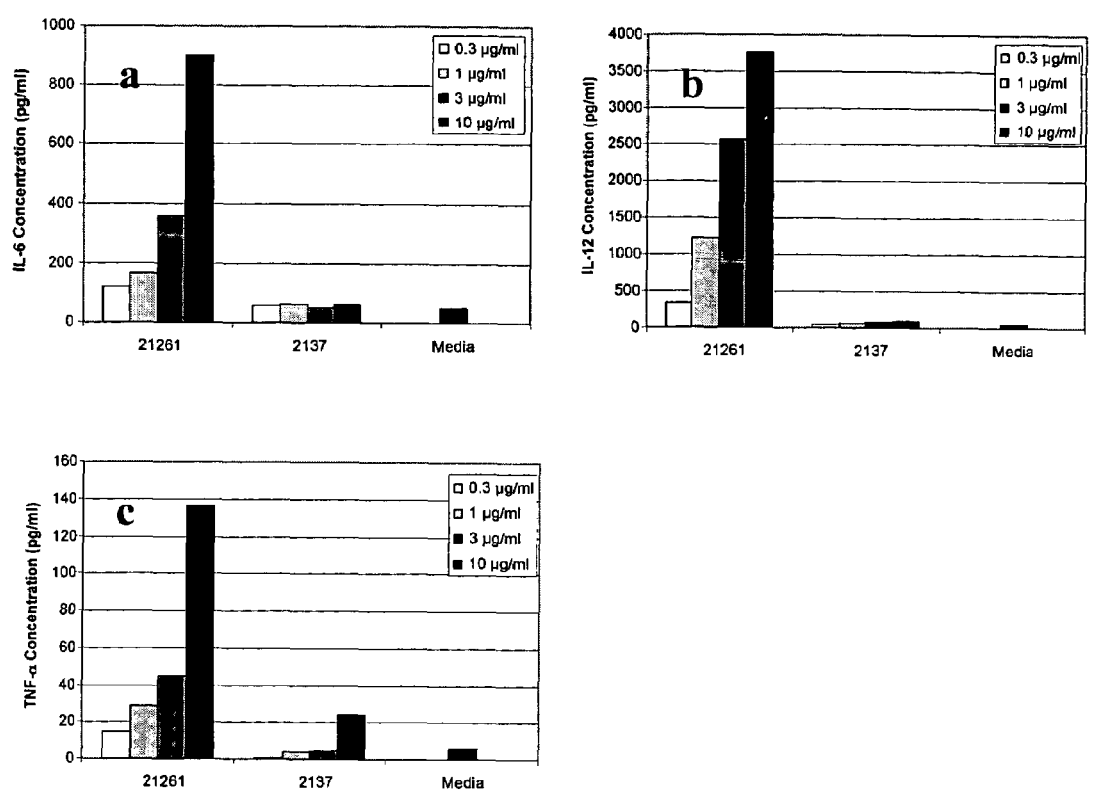

Figure 6: Lipophilic conjugates demonstrate *in vitro* TLR9$^{+/+}$ dependent IL-12 splenocyte stimulation.
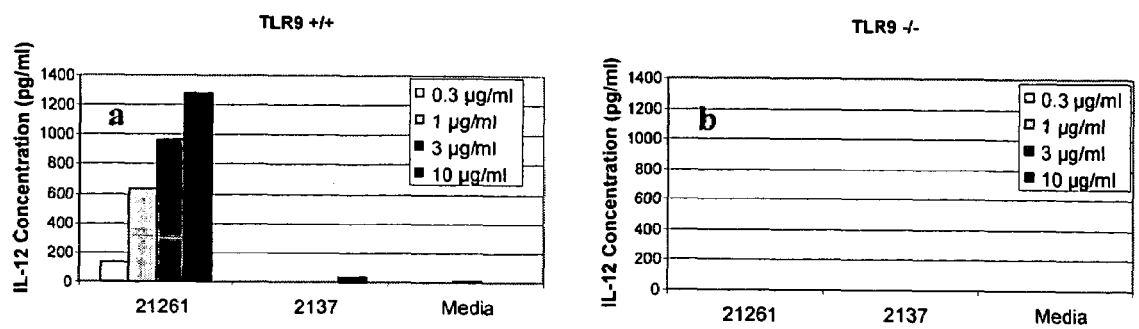

Figure 7: Lipophilic conjugates demonstrate *in vivo* time-dependent plasma IP-10 stimulation.
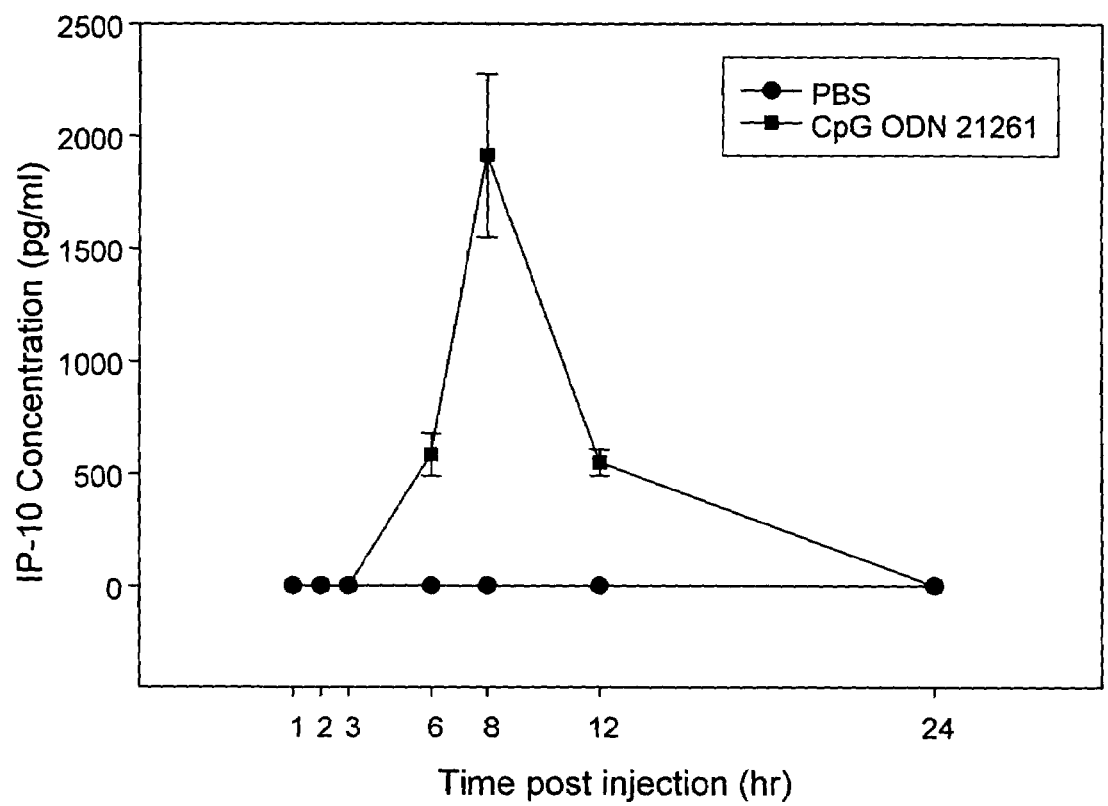

Figure 8: Lipophilic conjugates demonstrate *in vivo* plasma cytokine and chemokine stimulation of IP-10, IL-12 and IL-6 production.
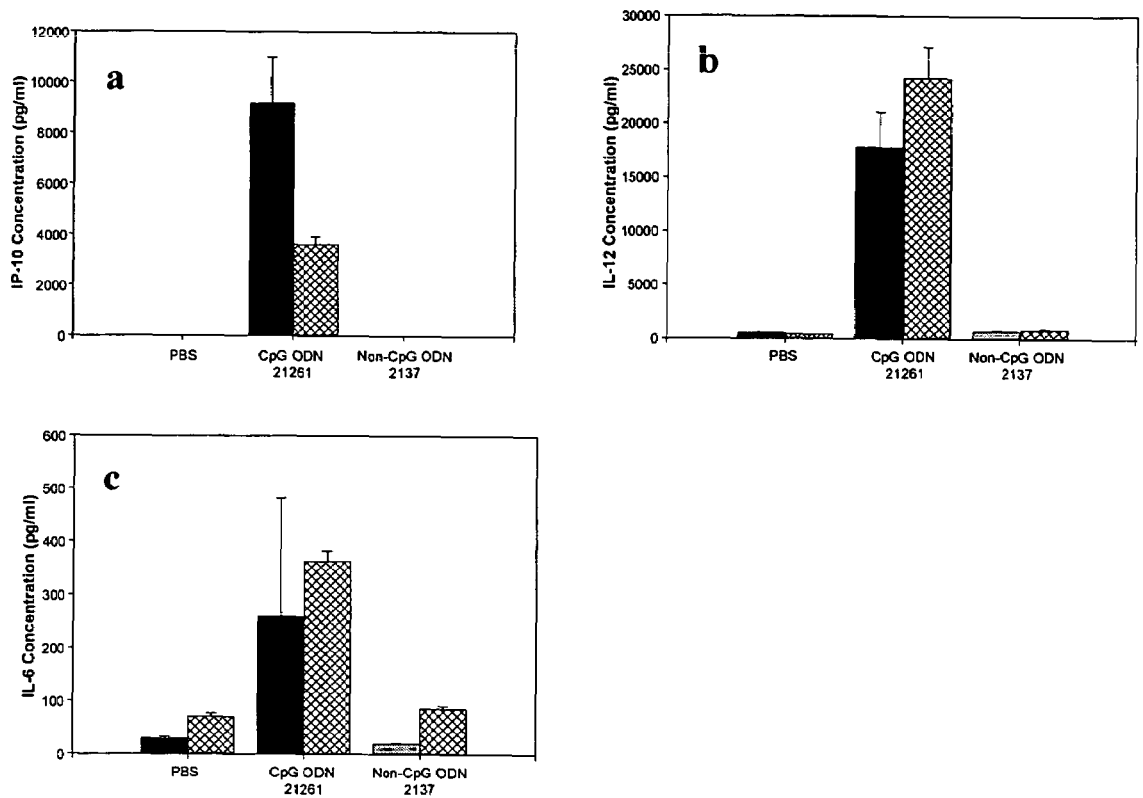

NUCLEIC ACID-LIPOPHILIC CONJUGATES

RELATED APPLICATIONS

This application claims priority under 35 U.S.C. § 119(e) to U.S. Provisional Application Ser. No. 60/505,977, filed Sep. 25, 2003 which is herein incorporated by reference in its entirety.

FIELD OF THE INVENTION

The present invention relates generally to nucleic acids-lipophilic conjugates, compositions thereof and methods of using the conjugates.

BACKGROUND OF THE INVENTION

Bacterial DNA has immune stimulatory effects to activate B cells and natural killer cells, but vertebrate DNA does not (Tokunaga, T., et al., 1988. *Jpn. J. Cancer Res.* 79:682-686; Tokunaga, T., et al., 1984, *JNCI* 72:955-962; Messina, J. P., et al., 1991, *J. Immunol.* 147:1759-1764; and reviewed in Krieg, 1998, In: Applied Oligonucleotide Technology, C. A. Stein and A. M. Krieg, (Eds.), John Wiley and Sons, Inc., New York, N.Y., pp. 431-448) and Krieg. A. M. CpG motifs in bacterial DNA and their immune effects (2002) Annu. Rev. Immunol. 20: 709-760. It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA (Krieg et al, 1995 Nature 374:546-549; Krieg, 1999 Biochim. Biophys. Acta 93321:1-10). The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-γ secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are dramatically reduced if the CpG motif is methylated, changed to a GpC, or otherwise eliminated or altered (Krieg et al, 1995 Nature 374:546-549; Hartmann et al, 1999 Proc. Natl. Acad. Sci USA 96:9305-10).

In early studies, it was thought that the immune stimulatory CpG motif followed the formula purine-purine-CpG-pyrimidine-pyrimidine (Krieg et al, 1995 Nature 374:546-549; Pisetsky, 1996 J. Immunol. 156:421-423; Hacker et al., 1998 EMBO J. 17:6230-6240; Lipford et al, 1998 Trends in Microbiol. 6:496-500). However, it is now clear that mouse lymphocytes respond quite well to phosphodiester CpG motifs that do not follow this "formula" (Yi et al., 1998 J. Immunol. 160:5898-5906) and the same is true of human B cells and dendritic cells (Hartmann et al, 1999 Proc. Natl. Acad. Sci USA 96:9305-10; Liang, 1996 J. Clin. Invest. 98:1119-1129). Nevertheless, the term "CpG motif" is generally used to refer to a hexamer motif in which the CpG dinucleotide is located at the center.

SUMMARY OF THE INVENTION

The present invention relates in part to immunostimulatory nucleic acids linked to a lipophilic group. It has been discovered that specific immunostimulatory nucleic acids linked to lipophilic groups have enhanced activity, whereas the linkage of lipophilic groups to other immunostimulatory nucleic acids has minimal effect on the immunostimulatory capability of the molecule.

The invention, in one aspect, relates to a composition of $(N_1PN_2)$ L, wherein $N_1$ and $N_2$ are independently nucleic acids of 0-100 nucleotides in length, P is a palindrome containing nucleic acid and comprising at least one YR dinucleotide, wherein Y is a cytosine or a modified cytosine and R is a guanine or a modified guanine, and wherein L is a lipophilic group. In one embodiment $N_1PN_2$ is 3-14 nucleotides in length. In another embodiment L is linked to the nucleotide at the 3' end of $N_1PN_2$. Optionally the nucleotide is selected from the group consisting of a nucleotide at the 3' end of $N_1PN_2$ and an internal nucleotide. In one embodiment P is 2-100 nucleotides in length. In another embodiment P is 4-14 nucleotides in length.

In other embodiments L is linked by a linker to a 2'-position of a nucleotide in $N_1PN_2$, to a heterocyclic base of a nucleotide in $N_1PN_2$, or a phosphodiester linkage in $N_1PN_2$.

L is a lipophilic group which is a cholesteryl, a modified cholesteryl, a cholesterol derivative, a reduced cholesterol, a substituted cholesterol, cholestan, C16 alkyl chain, bile acids, cholic acid, taurocholic acid, deoxycholate, oleyl litocholic acid, oleoyl cholenic acid, glycolipids, phospholipids, sphingolipids, isoprenoids, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. The composition may include at least 2 L.

In some embodiments the formula comprises $N_1PN_2$-L-$N_3PN_4$, wherein $N_3$ and $N_4$ are independently nucleic acids of 0-100 nucleotides in length. L may be linked to $N_1PN_2$ and $N_3PN_4$ through a linkage selected from the group consisting of -3'-L-3'-, -2'-L-2'-, -3'-L-2'- and -2'-L-3'-. In some embodiments $N_1PN_2$ and $N_3PN_4$ are identical. In other embodiments $N_1PN_2$ and $N_3PN_4$ are different.

The composition in other aspects of the invention is the following formula $([N_1PN_2]_n-(X_3)_m)\cdot(L)_p$. $X_3$ is a linker, m is an integer from 0 to 20 (preferably from 1-10), n is an integer from 0 to 20 (preferably from 1-10), and p is an integer from 1 to 10 (preferably 1). The oligonucleotide $N_1PN_2$ has a length of 4 to 40 nucleotides. n may be greater than 1 and the multiple $[N_1PN_2]$ are linked through 3'-ends.

In some embodiments $X_3$ is a non-nucleotidic linker selected from the group consisting of abasic residues (dSpacer), oligoethyleneglycol, such as triethyleneglycol (spacer 9) or hexaethylenegylcol (spacer 18), and alkane-diol, such as butanediol.

In other embodiments the linker is attached to the oligonucleotide through a linkage selected from the group consisting of phosphodiester, phosphorothioate, methylphosphonate, and amide linkages.

Optionally $N_1PN_2$ is a branched ODN and wherein $N_1$ includes at least one CG dinucleotide.

L may be attached to the 3' end of the oligonucleotide $[N_1PN_2]$. The linkage between L and $N_1PN_2$ may be metabolically stable or metabolically labile.

P may have the formula $X_1-Y-R-X_2$, wherein $X_1$ and $X_2$ are independently from 0 to 4 nucleotides. In some embodiments $X_1$ is 1 to 2 nucleotides. In other embodiments $X_1$ is a pyrimidine. Optionally the pyrimidine is selected from the group consisting of a thymidine, deoxyuridine and a 5-substituted deoxyuridine. In other embodiments $X_2$ is a palindrome or an inverted repeat (partial palindrome). The palindrome or inverted repeat (partial palindrome) may contain at least one unmethylated CpG motif. P may be selected from the group consisting of C_G_A_C, C_G_T_C, T_C_G_A_C, C_G_A_C_G_T_C, C_G_G_C_G_G_ and G_A_C_G_A.

In some embodiments the oligonucleotide $N_1PN_2$ has a length of 4 to 20 nucleotides or 6 to 14 nucleotides.

Optionally the oligonucleotide includes at least one linear or branched non-nucleoside linkage.

An immune stimulatory molecule may be associated with the composition. An example of an immune stimulatory molecule is a TLR9 ligand.

The oligonucleotide may include at least one stabilized internucleotide linkage. Preferably the stabilized internucleotide linkage is the linkage between Y and R and is a phosphorothioate linkage in an Rp configuration. Preferably the internucleotide linkages of the oligonucleotide are all phosphodiester linkages.

At least one nucleotide in the oligonucleotide may be a substituted or modified purine or pyrimidine. In one embodiment the substituted pyrimidine is a C5 substitution or the substituted purine is a C8 or C7 substitution. In another embodiment the substituted or modified purine or pyrimidine is selected from the group consisting of 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil), thymine derivatives (e.g. 2-thiothymine, 4-thiothymine, 6-substituted thymines), 7-deazaguanine, 7-deaza-7-substituted guanine (such as 7-deaza-7-(C2-C6)alkynylguanine), 7-deaza-8-substituted guanine, 7-deaza-8-aza guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. In another embodiment of the invention, the base is substituted by a universal base (e.g. 4-methylindole, 5-nitro-indole, 3-nitropyrrole, P-base, and K-base), an aromatic ring system (e.g. benzimidazole or dichlorobenzimidazole, 1-methyl-1H-[1,2,4]triazole-3-carboxylic acid amide) an aromatic ring system (e.g. fluorobenzene or difluorobenzene) and a hydrogen atom (dSpacer).

Multiple oligonucleotides may be linked by multiple doubler or trebler moieties and form a dendrimer.

The composition may include at least one amino acid residue linked by an amide linkage.

Optionally the oligonucleotide includes at least one internucleotide linkage selected from the group consisting of a 3'5'-, a 2'5'-, a 3'3'- and a 5'5'-linkage.

In one embodiment L is associated with a carrier. Optionally the carrier is selected from the group consisting of a liposome, ISCOM, a hydrophobic bead, a hydrophobic formulation, a polymer, a peptide, a protein, and a nucleic acid. The composition may also include a therapeutic agent.

The invention in other aspects is a composition that further comprises a nucleic acid having at least one exposed 5' end comprising, at least one YR dinucleotide, wherein Y is a cytosine or a modified cytosine and R is a guanine or a modified guanine, at least one single stranded region, at least one double stranded region and wherein the nucleic acid is linked to at least one lipophilic group.

The nucleic acid may be a single chain nucleic acid or have a double stranded region involving base pairing of at least two nucleic acids on each side of the double stranded region. In one embodiment the nucleic acid forms a double stranded region involving base pairing of at least three nucleic acids on each side of the double stranded region.

In some embodiments the nucleic acid is a branched nucleic acid.

In other embodiments the nucleic acid is two single chain nucleic acids at least partially hybridized to one another.

The nucleic acid may be linked to at least two lipophilic groups. Optionally the lipophilic group is linked to the nucleotide at the 3' end of the nucleic acid. In another aspect the invention is a lipophilic composition of $(N_1YRN_2)\cdot L$ wherein $N_1$ and $N_2$ are independently nucleic acids of 0-100 nucleotides in length, wherein Y is a cytosine or a modified cytosine and R is a guanine or a modified guanine, and $N_1YRN_2$ is at least 10 nucleotides in length. L is a lipophilic group linked to a 2'-position of a nucleotide in $N_1YRN_2$, or to a heterocyclic base of a nucleotide in $N_1YRN_2$. In one embodiment $N_1YRN_2$ is 5'TCCG3', 5'TTCG3' or 5'TCGTCG3'.

In yet another aspect, the invention is a composition of $(N_1PN_2)\cdot L$ wherein $N_1$ and $N_2$ are independently nucleic acids of 0-100 nucleotides in length, P is a palindromic containing nucleic acid and comprising at least one YR dinucleotide, wherein Y is a cytosine or a modified cytosine and R is a guanine or a modified guanine, and wherein L is cholesterol. In certain embodiments L is linked to the nucleotide at the 3' end of $N_1PN_2$. In certain embodiments $N_1PN_2$ is selected from the group consisting of 5'TCGACGTCGT3' (SEQ ID NO: 111) and 5'TCGACGTCGA3' SEQ ID NO: 112).

In another aspect, the invention relates to a method for treating allergy or asthma. The method is performed by administering to a subject having or at risk of having allergy or asthma an immunostimulatory CpG oligonucleotide described herein in an effective amount to treat allergy or asthma. In one embodiment the oligonucleotide is administered to a mucosal surface, such as a respiratory tissue. In other embodiments the oligonucleotide is administered in an aerosol formulation. Optionally the oligonucleotide is administered intranasally. In other embodiments the subject has or is at risk of developing allergic asthma.

A method for inducing cytokine production is provided according to another aspect of the invention. The method is performed by administering to a subject an immunostimulatory CpG oligonucleotide described herein in an effective amount to induce a cytokine selected from the group consisting of IP10, IL6, IL 8, IL12, IL18, TNF, IFN-α chemokines, and IFN-γ.

In another aspect the invention is a composition of the Lipophilic conjugates described herein in combination with an antigen or other therapeutic compound, such as an anti-microbial agent or an anti-cancer agent. The anti-microbial agent may be, for instance, an anti-viral agent, an anti-parasitic agent, an anti-bacterial agent or an anti-fungal agent.

The composition may optionally include a pharmaceutical carrier and/or be formulated in a delivery device. In some embodiments the delivery device is selected from the group consisting of cationic lipids, cell permeating proteins, and sustained release devices. In one embodiment the sustained release device is a biodegradable polymer or a microparticle.

According to another aspect of the invention a method of stimulating an immune response is provided. The method involves administering a Lipophilic conjugate to a subject in an amount effective to induce an immune response in the subject. Preferably the Lipophilic conjugate is administered orally, locally, in a sustained release device, mucosally, systemically, parenterally, or intramuscularly. When the Lipophilic conjugate is administered to the mucosal surface it may be delivered in an amount effective for inducing a mucosal immune response or a systemic immune response. In preferred embodiments the mucosal surface is an oral, nasal, rectal, vaginal, or ocular surface.

In some embodiments the method includes exposing the subject to an antigen wherein the immune response is an antigen-specific immune response. In some embodiments the antigen is selected from the group consisting of a tumor antigen, a viral antigen, a bacterial antigen, a parasitic antigen and a peptide antigen.

CpG immunostimulatory oligonucleotides are capable of provoking a broad spectrum of immune response. For instance these Lipophilic conjugates can be used to redirect a Th2 to a Th1 immune response. Lipophilic conjugates may also be used to activate an immune cell, such as a lymphocyte (e.g., B and T cells), a dendritic cell, and an NK cell. The activation can be performed in vivo, in vitro, or ex vivo, i.e., by isolating an immune cell from the subject, contacting the immune cell with an effective amount to activate the immune cell of the Lipophilic conjugate and re-administering the activated immune cell to the subject. In some embodiments the dendritic cell presents a cancer antigen. The dendritic cell can be exposed to the cancer antigen ex vivo.

The immune response produced by Lipophilic conjugates may also result in induction of cytokine production, e.g., production of IP10, IL6, IL 8, IL12, IL18, TNF, IFN-$\alpha$, chemokines, and IFN-$\gamma$.

In still another embodiment, the Lipophilic conjugates are useful for treating cancer in a subject having or at risk of developing a cancer. The cancer may be selected from the group consisting of biliary tract cancer, breast cancer, cervical cancer, choriocarcinoma, colon cancer, endometrial cancer, gastric cancer, intraepithelial neoplasms, lymphomas, liver cancer, lung cancer (e.g. small cell and non-small cell), melanoma, neuroblastomas, oral cancer, ovarian cancer, pancreatic cancer, prostate cancer, rectal cancer, sarcomas, thyroid cancer, and renal cancer, as well as other carcinomas and sarcomas. In some important embodiments, the cancer is selected from the group consisting of bone cancer, brain and CNS cancer, connective tissue cancer, esophageal cancer, eye cancer, Hodgkin's lymphoma, larynx cancer, oral cavity cancer, skin cancer, and testicular cancer.

Lipophilic conjugates may also be used for increasing the responsiveness of a cancer cell to a cancer therapy (i.e., an anti-cancer therapy), optionally when the Lipophilic conjugate is administered in conjunction with an anti-cancer therapy. The anti-cancer therapy may be, for instance, a chemotherapy, a vaccine (e.g., an in vitro primed dendritic cell vaccine or a cancer antigen vaccine) or an immunotherapeutic agent such as an antibody based therapy. This latter therapy may also involve administering an antibody specific for a cell surface antigen of, for example, a cancer cell, wherein the immune response results in antibody dependent cellular cytotoxicity (ADCC). In one embodiment, the antibody may be selected from the group consisting of Ributaxin, HERCEPTIN®, QUADRAMET®, Panorex, IDEC-Y2B8, BEC2, C225, ONCOLYM®, SMART™ M195, ATRAGEN®, OVAREX®, BEXXAR®, LDP-03, ior t6, MDX-210, MDX-11, MDX-22, OV103, 3622W94, anti-VEGF, ZENAPAX®, MDX-220, MDX-447, MELIMMUNE-2, MELIMMUNE-1, CEACIDE®, PRETARGET®, NovoMAb-G2, TNT, Gliomab-H, GNI-250, EMD-72000, LYMPHOCIDE®, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA.

Thus, according to some aspects of the invention, a subject having cancer or at risk of having a cancer is administered a Lipophilic conjugate and an anti-cancer therapy. In some embodiments, the anti-cancer therapy is selected from the group consisting of a chemotherapeutic agent, an immunotherapeutic agent and a cancer vaccine.

In still another embodiment of the methods directed to treating cancer, the subject may be further administered interferon-$\alpha$.

In other aspects, the invention is a method for inducing an innate immune response by administering to the subject a Lipophilic conjugate in an amount effective for activating an innate immune response. Thus the ODN are useful for treating pathogens such as Leishmania, Listeria, and Anthrax.

According to another aspect of the invention a method for treating a viral or retroviral infection is provided. The method involves administering to a subject having or at risk of having a viral or retroviral infection, an effective amount for treating the viral or retroviral infection of any of the compositions of the invention. In some embodiments the virus is caused by hepatitis virus e.g., hepatitis B or hepatitis C, HIV, herpes virus, or papillomavirus.

A method for treating a bacterial infection is provided according to another aspect of the invention. The method involves administering to a subject having or at risk of having a bacterial infection, an effective amount for treating the bacterial infection of any of the compositions of the invention. In one embodiment the bacterial infection is due to an intracellular bacteria.

In another aspect the invention is a method for treating a parasite infection by administering to a subject having or at risk of having a parasite infection, an effective amount for treating the parasite infection of any of the compositions of the invention. In one embodiment the parasite infection is due to an intracellular parasite. In another embodiment the parasite infection is due to a non-helminthic parasite.

In some embodiments the subject is a human and in other embodiments the subject is a non-human vertebrate such as a dog, cat, horse, cow, pig, turkey, goat, fish, monkey, chicken, rat, mouse, or sheep.

In another aspect the invention relates to a method for inducing a TH1 immune response by administering to a subject any of the compositions of the invention in an effective amount to produce a TH1 immune response.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

The present invention may be more easily and completely understood when taken in conjunction with the accompanying figures.

FIG. 1 is a graph depicting the effect of linkage of a lipophilic group to an immunostimulatory nucleic acid through induction of IFN-$\alpha$.

FIG. 2 is a bar graph depicting effect of linkage of a lipophilic group to an immunostimulatory nucleic acid through induction of IL-6.

FIG. 3 is a bar graph depicting effect of linkage of a lipophilic group to an immunostimulatory nucleic acid through induction of IL-10.

FIG. 4 is a bar graph demonstrating that a lipophilic group conjugated to an immunostimulatory nucleic acid enhances induction of TLR9-dependent NF☐FB signaling.

FIG. 5 is a bar graph depicting the in vitro mouse splenocyte stimulation effect of linkage of a lipophilic group to an immunostimulatory nucleic acid through induction of IL-6, IL-12, and TNF-α.

FIG. 6 is a bar graph depicting the in vitro TLR9$^{+/+}$ and TLR9$^{-/-}$ mouse splenocyte stimulation effect of linkage of a lipophilic group to an immunostimulatory nucleic acid through induction of IL-12.

FIG. 7 is a graph depicting the in vivo time-dependent effect of linkage of a lipophilic group to an immunostimulatory nucleic acid through induction of IP-10.

FIG. 8 is a bar graph depicting the in vivo stimulation effect of linkage of a lipophilic group to an immunostimulatory nucleic acid through induction of IP-10, IL-12 and IL-6.

DETAILED DESCRIPTION

The invention in one aspect involves the finding that specific sub-classes of immunostimulatory oligonucleotides linked to a lipophilic group are highly effective in mediating immune stimulatory effects. These conjugates are useful therapeutically and prophylactically for stimulating the immune system to treat cancer, infectious diseases, allergy, asthma and other disorders.

A-Class immunostimulatory CpG oligonucleotides, such as oligonucleotide SEQ ID NO: 40, are characterized by their very efficient induction of IFN-α secretion, but low B cell stimulation. SEQ ID NO: 40 is composed of a palindromic phosphodiester CpG sequence (SEQ ID NO: 110) clamped by phosphorothioate (G)n stretches. ODN sequences are presented in Table 1 below. A-Class immunostimulatory CpG oligonucleotides, in which the 3'- and 5'-ends are phosphorothioate-modified and the center portion is phosphodiester, have runs of at least four G residues at both ends of the oligonucleotide. As a result of intermolecular tetrad formation which results in high molecular weight aggregates, the development of G-rich oligonucleotides has been difficult. Issues related to the biophysical properties of this class of compounds include tendency to aggregation, poor solubility, difficulty in quality control and solid phase extraction (SPE) used in PK studies.

It is known that (G)n stretches in oligonucleotides, where n≧4, lead to intermolecular tetrad formation resulting in non homogeneous high molecular weight aggregates. The uptake of oligonucleotides with (G)n stretches is about 20 to 40-times higher than of non-aggregated oligonucleotides and the intracellular localization appears also to be different. It is not understood how these observations correlate with biological activity.

In an attempt to discover new immunostimulatory oligonucleotides having similar potency to A-class oligonucleotides such as SEQ ID NO: 40 but more favorable biophysical properties than G-rich oligonucleotides, a series of oligonucleotides without (G)n stretches but having lipophilic residues covalently attached have been developed according to the invention. Surprisingly, high Interferon-alpha (IFN-α) induction was detected, when an oligonucleotide having a palindromic center region, preferably with phosphodiester linkages, and at least one lipophilic group attached, even without the G$_n$ sequences believed to be critical for A-class activity. For highest IFN-α induction, it is preferable that the number of phosphorothioate residues is kept to a minimum. An unexpectedly high induction of IFN-α secretion was observed with compositions composed of an L (lipophilic group) attached to the 3'-end of an oligonucleotide with a 5'-TCG and having only few or no phosphorothioate linkages.

It is also of interest that B-Class CpG oligonucleotides, when modified at the 3'-end with Cholesterol (SEQ ID NO: 38), are less immunostimulatory than the corresponding 3'-unmodified (SEQ ID NO: 36) both in IFN-α induction and in a TLR9 assay. Similarly, the activity of a 5'-Cholesterol modified ODN (SEQ ID NO: 37) is much lower than that of the 5'-unmodified SEQ ID NO: 36. B-class ODN consist of non-palindromic sequences and are usually fully phosphorothioate modified. The decreased activity of B-class CpG ODN resulting from cholesterol modification is in contrast to the palindromic phosphodiester CpG ODN described herein. Cholesterol modification of the latter at the 3'-end results in increased immunostimulatory activity (SEQ ID NO: 4) while 5'-cholesterol modification of the same sequence completely abolishes activity (SEQ ID NO: 6).

In some instances non-palindromic YR containing oligonucleotides having phosphodiester backbones also have increased immune stimulatory activity when a lipophilic group is conjugated at the 3' end of the oligonucleotide. Chimeric oligonucleotides having at least one YR motif that is phosphodiester but having at least one phosphorothioate or other modified linkage at the 5' and 3' end of the oligonucleotide also have increased immune stimulatory activity if a lipophilic group is conjugated at the 3' end of the molecule. The YR motifs in such chimeric oligonucleotides may be palindromic or nonpalindromic.

Thus, the invention involves, in one aspect, the discovery that a subset of immunostimulatory oligonucleotides linked to lipophilic groups have improved immune stimulatory properties. In some aspects the invention is a conjugate having the following formula (N$_1$PN$_2$)·L. L is a lipophilic group.

The lipophilic group L is preferably a cholesterol, a cholesteryl or modified cholesteryl residue. The cholesterol moiety may be reduced (e.g. as in cholestan) or may be substituted (e.g. by halogen). A combination of different lipophilic groups in one molecule is also possible. Other lipophilic groups include but are not limited to bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. In some embodiments L is not a cholesterol.

The highest immunostimulatory activity was brought about by cholesterol modification as compared to other end-modifications, such as hexedecyl, vitamin E or triethylenglycole. It is expected, however, that these agents will produce more activity when more than one agent is attached to an oligonucleotide. Thus, in some embodiments the compositions of the invention have multiple L groups.

L is preferably at or near the 3' end of the oligonucleotide, unless it is in a branched oligonucleotide where there is at least one unobstructed 5' CpG motif. Cholesterol substitution at the only available 5'-end of the oligonucleotides tested was detrimental to the immunostimulatory effect (SEQ ID NO: 5 and SEQ ID NO: 6).

L may be connected to the oligonucleotide by a linker moiety. Optionally the linker moiety is a non-nucleotidic linker moiety. Non-nucleotidic linkers are e.g. abasic residues (dSpacer), oligoethyleneglycol, such as triethyleneglycol (spacer 9) or hexaethyleneglycol (spacer 18), or alkane-diol, such as butanediol. The spacer units are preferably linked by phosphodiester or phosphorothioate bonds. The linker units may appear just once in the molecule or may be incorporated several times, e.g. via phosphodiester, phosphorothioate, methylphosphonate, or amide linkages.

The lipophilic group L may be attached at various positions of the oligonucleotide. As described above, the lipophilic group L is linked to the 3'-end of the oligonucleotide, where it also serves the purpose to enhance the stability of the oligomer against 3'-exonucleases. Alternatively, it may be linked to an internal nucleotide or a nucleotide on a branch. The lipophilic group L may be attached to a 2'-position of the nucleotide. The lipophilic group L may also be linked to the heterocyclic base of the nucleotide.

The oligonucleotides may have one or more than one accessible 5' ends. This may be achieved, for instance by attaching two oligonucleotides through a 3'-3' or other linkage or to connect two 3' ends through an L group to generate an oligonucleotide having one or two accessible 5' ends. Such a structure might have a formula such as 5'TCGN$_1$—L—N$_1$GCT5'. The 3'3'-linkage may be, for instance, a phosphodiester, phosphorothioate or any other modified internucleoside bridge. Methods for accomplishing such linkages are known in the art. For instance, such linkages have been described in Seliger, H.; et al., Oligonucleotide analogs with terminal 3'-3'- and 5'-5'-internucleotidic linkages as antisense inhibitors of viral gene expression, Nucleosides & Nucleotides (1991), 10(1-3), 469-77 and Jiang, et al., Pseudo-cyclic oligonucleotides: in vitro and in vivo properties, Bioorganic & Medicinal Chemistry (1999), 7(12), 2727-2735.

Additionally, 3'3'-linked ODNs where the linkage between the 3'-terminal nucleosides is not a phosphodiester, phosphorothioate or other modified bridge, can be prepared using an additional spacer, such as tri- or tetra-ethylenglycol phosphate moiety (Durand, M. et al, Triple-helix formation by an oligonucleotide containing one (dA)12 and two (dT)12 sequences bridged by two hexaethylene glycol chains, Biochemistry (1992), 31(38), 9197-204, U.S. Pat. No. 5,658,738, and U.S. Pat. No. 5,668,265). Alternatively, the non-nucleotidic linker may be derived from ethanediol, propanediol, or from an abasic deoxyribose (dSpacer) unit (Fontanel, Marie Laurence et al., Sterical recognition by T4 polynucleotide kinase of non-nucleosidic moieties 5'-attached to oligonucleotides; Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

Further preferred are oligonucleotides of the formula in which the lipophilic modification is part of the inter-nucleotide linkage which connects two adjacent nucleosides. If the lipophilic residue is within the sequence, thus linking different sequence parts together, then the sequence parts are preferentially not connected via their 5'-ends. In this case, two or more 3'3'-linked sequences are preferred. Also preferred are 2'2'-, 3'2'- or 2'3'-linked sequences, respectively. Optionally the linkage could be a 5'3' linkage. If two or more sequences are linked, these can be identical or different. Preferred linkages are phosphodiester, phosphorothioate, amide, ether, thioether, urea, thiourea, sulfonamide, Schiff Base and disulfide linkages. Another possibility is the use of the Solulink BioConjugation System.

The lipophilic group may be linked to the oligonucleotide without additional spacers (m=0) or can be linked via one or more linker units (m>1). The linkage between the oligonucleotide and the lipophilic residue may be a metabolically stable or metabolically labile one.

Thus, in some embodiments the conjugate may have the following formula:

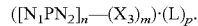

N$_1$ and N$_2$ are independently nucleic acids of 0-100 nucleotides in length, P is a palindromic containing nucleic acid and comprising at least one YR dinucleotide, wherein Y is a cytosine or a modified cytosine and R is a guanine or a modified guanine.

N may optionally have interspersed linear or branched non-nucleoside linkages or other immune stimulatory conjugates such as ligands for TLR molecules. It has been discovered that oligonucleotides having a 5'TCG or 5' UCG have particularly strong immunostimulatory capability.

The oligonucleotide of the formula (separate from the linkers connecting nucleotides to L) may also contain non-nucleotidic linkers, in particular abasic linkers (dSpacers), triethylene glycol units or hexaethylene glycol units. Further preferred linkers are alkylamino linkers, such as C3, C6, C12 aminolinkers, and also alkylthiol linkers, such as C3 or C6 thiol linkers. Oligonucleotides with a 3'3'-linkage may also contain a Doubler or Trebler unit. Branching of the oligonucleotides by multiple doubler or trebler moieties leads to dendrimers which are a further embodiment of this invention. The oligonucleotide of formula I may also contain linker units resulting from peptide modifying reagents or oligonucleotide modifying reagents. Furthermore, it may contain one or more natural or unnatural amino acid residues which are connected by peptide (amide) linkages. The nucleotides in the formula may be linked through 3'5'- and/or 2'5'-linkages. It may further contain independently from each other one or more 3'3'-linkages and/or 5'5'-linkages.

P is a palindrome or inverted repeat, i.e. a partial palindrome. Preferably, the palindrome or inverted repeat (partial palindrome) contains at least one unmethylated CpG motif. In some embodiments it includes at least 2 or 3 CpG motifs. In SEQ ID NO: 4, the sequence (TCGACGTCGT, SEQ ID NO: 111) is only partially palindromic (CGACGTCG), i.e. inverted repeat, whereas in SEQ ID NO: 13, the sequence forms a complete palindrome. Preferably, at least one of the CpG motifs in the palindrome or inverted repeat (partial palindrome) is TCGA, ACGT, or CGGCCG. Some preferred palindromes include:

| | |
|---|---|
| C G A C G T C G | |
| C G T C G A C G | |
| T C G A C G T C G A | SEQ ID NO: 112 |
| C G A C G T C G A C G T C G | SEQ ID NO: 113 |
| C G G C G G C C G C C G | SEQ ID NO: 114 |
| G A C G A T C G T C | SEQ ID NO: 115 |

The immunostimulatory oligonucleotides generally have a length in the range of between 4 and 100 nucleotides. In some embodiments the length is in the range of 4-40, 13-100, 13-40, 13-30, 15-50, or 15-30 nucleotides or any integer range therebetween.

The terms "nucleic acid" and "oligonucleotide" are used interchangeably to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the terms "nucleic acid" and "oligonucleotide" refer to oligoribonucleotides as well as oligodeoxyribonucleotides. The terms "nucleic acid" and "oligonucleotide" shall also include polynucleosides (i.e., a polynucleotide minus the phosphate) and any other organic base containing polymer. Nucleic acid molecules can be obtained from existing nucleic acid sources (e.g., genomic or cDNA), but are preferably synthetic (e.g., produced by nucleic acid synthesis). The term oligonucleotide generally refers to a shorter molecule, i.e. 100 nucleotides or less in length.

The terms "nucleic acid" and "oligonucleotide" also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated ribose group. In addition, modified nucleic acids may include sugars such as arabinose or 2'-fluoroarabinose instead of ribose. Thus the nucleic acids may be heterogeneous in backbone composition thereby containing any possible combination of polymer units linked together such as peptide-nucleic acids (which have an amino acid backbone with nucleic acid bases). Other examples are described in more detail below.

The immunostimulatory oligonucleotides of the instant invention can encompass various chemical modifications and substitutions, in comparison to natural RNA and DNA, involving a phosphodiester internucleoside bridge, a β-D-ribose unit and/or a natural nucleoside base (adenine, guanine, cytosine, thymine, uracil). Examples of chemical modifications are known to the skilled person and are described, for example, in Uhlmann E et al. (1990) *Chem Rev* 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) *Annu Rev Pharmacol Toxicol* 36:107-129; and Hunziker J et al. (1995) *Mod Synth Methods* 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

For example, the oligonucleotides may comprise one or more modifications and wherein each modification is independently selected from:
a) the replacement of a phosphodiester internucleoside bridge located at the 3' and/or the 5' end of a nucleoside by a modified internucleoside bridge,
b) the replacement of phosphodiester bridge located at the 3' and/or the 5' end of a nucleoside by a dephospho bridge,
c) the replacement of a sugar phosphate unit from the sugar phosphate backbone by another unit,
d) the replacement of a β-D-ribose unit by a modified sugar unit, and
e) the replacement of a natural nucleoside base by a modified nucleoside base.

More detailed examples for the chemical modification of an oligonucleotide are as follows.

The oligonucleotides may include modified internucleotide linkages, such as those described in a or b above. These modified linkages may be partially resistant to degradation (e.g., are stabilized). A "stabilized oligonucleotide molecule" shall mean an oligonucleotide that is relatively resistant to in vivo degradation (e.g. via an exo- or endo-nuclease) resulting form such modifications. Oligonucleotides having phosphorothioate linkages, in some embodiments, may provide maximal activity and protect the oligonucleotide from degradation by intracellular exo- and endo-nucleases.

A phosphodiester internucleoside bridge located at the 3' and/or the 5' end of a nucleoside can be replaced by a modified internucleoside bridge, wherein the modified internucleoside bridge is for example selected from phosphorothioate, phosphorodithioate, $NR^1R^2$-phosphoramidate, boranophosphate, α-hydroxybenzyl phosphonate, phosphate-$(C_1$-$C_{21})$-O-alkyl ester, phosphate-$[(C_6$-$C_{12})$aryl-$(C_1$-$C_{21})$-O-alkyl]ester, $(C_1$-$C_8)$alkylphosphonate and/or $(C_6$-$C_{12})$arylphosphonate bridges, $(C_7$-$C_{12})$-☐-hydroxymethyl-aryl (e.g., disclosed in WO 95/01363), wherein $(C_6$-$C_{12})$aryl, $(C_6$-$C_{20})$aryl and $(C_6$-$C_{14})$aryl are optionally substituted by halogen, alkyl, alkoxy, nitro, cyano, and where $R^1$ and $R^2$ are, independently of each other, hydrogen, $(C_1$-$C_{18})$-alkyl, $(C_6$-$C_{20})$-aryl, $(C_6$-$C_{14})$-aryl-$(C_1$-$C_8)$-alkyl, preferably hydrogen, $(C_1$-$C_8)$-alkyl, preferably $(C_1$-$C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleoside by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

A sugar phosphate unit (i.e., a β-D-ribose and phosphodiester internucleoside bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al. (1989) *Nucleic Acids Res* 17:6129-41), that is, e.g., the replacement by a morpholino-derivative unit; or to build up a polyamide nucleic acid ("PNA"; as described for example, in Nielsen P E et al. (1994) *Bioconjug Chem* 5:3-7), that is, e.g., the replacement by a PNA backbone unit, e.g., by 2-aminoethylglycine. The oligonucleotide may have other carbohydrate backbone modifications and replacements, such as peptide nucleic acids with phosphate groups (PHONA), locked nucleic acids (LNA), and oligonucleotides having backbone sections with alkyl linkers or amino linkers. The alkyl linker may be branched or unbranched, substituted or unsubstituted, and chirally pure or a racemic mixture.

A β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, 2'-O-$(C_1$-$C_6)$alkyl-ribose, preferably 2'-O-$(C_1$-$C_6)$ alkyl-ribose is 2'-O-methylribose, 2'-O-$(C_2$-$C_6)$alkenyl-ribose, 2'-[O-$(C_1$-$C_6)$alkyl-O-$(C_1$-$C_6)$alkyl]-ribose, 2'-$NH_2$-2'-deoxyribose, β-D-xylo-furanose, α-arabinofuranose, 2,4-dideoxy-β-D-erythro-hexo-pyranose, and carbocyclic (described, for example, in Froehler J (1992) *Am Chem Soc* 114:8320) and/or open-chain sugar analogs (described, for example, in Vandendriessche et al. (1993) *Tetrahedron*

49:7223) and/or bicyclosugar analogs (described, for example, in Tarkov M et al. (1993) *Helv Chim Acta* 76:481).

In some embodiments the sugar is 2'-O-methylribose, particularly for one or both nucleotides linked by a phosphodiester or phosphodiester-like internucleoside linkage.

Nucleic acids also include substituted purines and pyrimidines such as C-5 propyne pyrimidine and 7-deaza-7-substituted purine modified bases. Wagner R W et al. (1996) *Nat Biotechnol* 14:840-4. Purines and pyrimidines include but are not limited to adenine, cytosine, guanine, and thymine, and other naturally and non-naturally occurring nucleobases, substituted and unsubstituted aromatic moieties.

A modified base is any base which is chemically distinct from the naturally occurring bases typically found in DNA and RNA such as T, C, G, A, and U, but which share basic chemical structures with these naturally occurring bases. The modified nucleoside base may be, for example, selected from hypoxanthine, uracil, dihydrouracil, pseudouracil, 2-thiouracil, 4-thiouracil, 5-aminouracil, 5-($C_1$-$C_6$)-alkyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleosides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleoside bases. This list is meant to be exemplary and is not to be interpreted to be limiting.

In particular formulas described herein a set of modified bases is defined. For instance the letter Y is used to refer to a nucleotide containing a cytosine or a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluorouracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g. 3-nitropyrrole, P-base), an aromatic ring system (e.g. fluorobenzene or difluorobenzene) or a hydrogen atom (dSpacer).

The letter R is used to refer to guanine or a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-(C2-C6) alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. In another embodiment of the invention, the guanine base is substituted by a universal base (e.g. 4-methyl-indole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom (dSpacer).

Certain base modifications were also allowed. SEQ ID NO: 29, in which the terminal T residues at either end were replaced by deoxyuridine (U), turned out to be a potent inducer of IFN-α. In contrast, replacing G by deoxyinosine (I) in all CpG motifs (as in SEQ ID NO: 30) completely abolished IFN-α induction. Surprisingly, modification of G residues as 7-deaza deoxyguanosine (SEQ ID NO: 31) resulted in high IFN-α induction. Therefore, the need for tetrad formation via Hoogsteen base-pairing, a prerequisite for high activity of the previously described G-rich A-Class oligonucleotides, can be excluded for the new cholesterol modified A-Class immunostimulatory oligonucleotides.

For use in the instant invention, the oligonucleotides of the invention can be synthesized de novo using any of a number of procedures well known in the art. For example, the β-cyanoethyl phosphoramidite method (Beaucage, S. L., and Caruthers, M. H., *Tet. Let.* 22:1859, 1981); nucleoside H-phosphonate method (Garegg et al., *Tet. Let.* 27:4051-4054, 1986; Froehler et al., *Nucl. Acid. Res.* 14:5399-5407, 1986, ; Garegg et al., *Tet. Let.* 27:4055-4058, 1986, Gaffney et al., *Tet. Let.* 29:2619-2622, 1988). These chemistries can be performed by a variety of automated nucleic acid synthesizers available in the market. These oligonucleotides are referred to as synthetic oligonucleotides. An isolated oligonucleotide generally refers to an oligonucleotide which is separated from components which it is normally associated with in nature. As an example, an isolated oligonucleotide may be one which is separated from a cell, from a nucleus, from mitochondria or from chromatin.

The internucleotide linkages in the oligonucleotide, may be a non-stabilized or stabilized linkage (against nucleases), preferably a phosphodiester (non stabilized), a phosphorothioate (stabilized) or another charged backbone, most preferably a phosphodiester linkage. If the internucleotide linkage at Y-R is a phosphorothioate, the chirality of this linkage may be random, or is preferably a phosphorothioate linkage of Rp configuration. Increasing numbers of phosphorothioate linkages (SEQ ID NO: 3, SEQ ID NO: 15, SEQ ID NO: 25), in particular at the 5'-end, resulted in diminished or no IFN-α induction.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (e.g., Uhlmann, E. and Peyman, A., *Chem. Rev.* 90:544, 1990; Goodchild, J., *Bioconjugate Chem.* 1:165, 1990).

TABLE 1

| ODN # | Sequence |
|---|---|
| SEQ ID NO: 1 | **T*C**_G_A_C_G_T_C_G_T_teg |
| SEQ ID NO: 2 | **T*C**_G_A_C_G_T_C_G_T_L |
| SEQ ID NO: 3 | **T*C_G_A_C_G_T_C_G*T**-Chol |
| SEQ ID NO: 4 | T_C_G_A_C_G_T_C_G_T_Chol |
| SEQ ID NO: 5 | Chol-T_C_G_A_C_G_T_C_G_T-Chol |
| SEQ ID NO: 6 | Chol_T_C_G_A_C_G_T_C_G_T_teg |
| SEQ ID NO: 7 | T_C_G_T_C_G_A_C_G_T_G_Chol |
| SEQ ID NO: 8 | T_C_G_A_C_G_T_C_G_T_T_Chol |
| SEQ ID NO: 9 | G_T_C_G_A_C_G_T_C_G_T_Chol |
| SEQ ID NO: 10 | G_T_C_G_A_C_G_T_C_G_T_T_Chol |
| SEQ ID NO: 11 | T_C_G_T_C_G_A_C_G_T_T_Chol |
| SEQ ID NO: 12 | A_C_G_A_C_G_T_C_G_T_Chol |
| SEQ ID NO: 13 | T_C_G_A_C_G_T_C_G_A_Chol |
| SEQ ID NO: 14 | G_A_C_G_A_C_G_T_C_G_T_T_Chol |
| SEQ ID NO: 15 | **T*C*G*A*C*G*T*C*G*T**_Chol |
| SEQ ID NO: 16 | **T*C**_G_A_C_G_T_C_G_T_Chol |
| SEQ ID NO: 17 | T_C_G_A_C_G_T_C_G*T_Chol |
| SEQ ID NO: 18 | T_C_G_A_C_G_T_C_G_T_teg |
| SEQ ID NO: 19 | T_C_G_A_C_G_T_C_G_A_C_G_T_C_G_T_Chol |
| SEQ ID NO: 20 | T_C_G_T_C_G_T_C_G_T_Chol |
| SEQ ID NO: 21 | T_G_C_A_G_C_T_G_C_T-Chol |
| SEQ ID NO: 22 | ..C_G_A_C_G_T_C_G..._Chol |
| SEQ ID NO: 23 | T_A_A_C_G_T_T_T_Chol |
| SEQ ID NO: 24 | T_G_A_C_G_T_T_T_Chol |
| SEQ ID NO: 25 | **T*C*G*T**_C_G_A_C_G_T_C_G_T_Chol |
| SEQ ID NO: 26 | **T*C*G*T*C*G*T*T*T*T**_T_C_G_A_C_G_T_C_G_T_Chol |
| SEQ ID NO: 27 | T_C_G_G_C_G_G_C_C_G_C_C_G_Chol |
| SEQ ID NO: 28 | **T*C*G*T**_C_G_G_C_G_G_C_C_G_C_C_G_T_Chol |
| SEQ ID NO: 29 | U_C_G_A_C_G_T_C_G_U-Chol |
| SEQ ID NO: 30 | T_C_I_A_C_I_T_C_I_T-Chol |
| SEQ ID NO: 31 | T_C_7_A_C_7_T_C_7_T-Chol |
| SEQ ID NO: 32 | T_C_A_T_C_G_A_T_G_A_Chol |
| SEQ ID NO: 33 | ....G_A_C_G_A_T_C_G_T_C_Chol |
| SEQ ID NO: 34 | T_C_A_C_C_G_G_T_G_A_Chol |
| SEQ ID NO: 35 | G_A_C_G_T_T_A_A_C_G_T_C_Chol |
| SEQ ID NO: 36 | **T*C*G*T*C*G*T*T*T*T*G*T*C*G*T*T*T*T*G*T*C*G*T*T** (B-Class ODN) |
| SEQ ID NO: 37 | Chol_**T*C*G*T*C*G*T*T*T*T*G*T*C*G*T*T*T*T*G*T*C*G*T*T** |
| SEQ ID NO: 38 | **T*C*G*T*C*G*T*T*T*T*G*T*C*G*T*T*T*T*G*T*C*G*T*T**_Chol |
| SEQ ID NO: 39 | **T*C*G*T*C*G*T*T*T*T*C*G*G*C*G*C*G*C*G*C*C*G** (C-Class ODN) |
| SEQ ID NO: 40 | **G*G*G_G_A_C_G_A_C_G_T_C_G_T_G_G*G*G*G*G** (A-Class ODN) |
| SEQ ID NO: 41 | T_C_G_A_Chol |
| SEQ ID NO: 42 | T_C_G_C_G_A_Chol |
| SEQ ID NO: 43 | T_C_G_C_G_C_G_A_Chol |
| SEQ ID NO: 44 | T_C_G_C_C_G_G_C_G_A_Chol |
| SEQ ID NO: 45 | T_C_G_G_C_G_C_C_G_A_Chol |
| SEQ ID NO: 46 | T_C_G_C_G_C_G_C_G_A_Chol |
| SEQ ID NO: 47 | T_C_G_T_C_G_A_C_G_A_Chol |
| SEQ ID NO: 48 | T_C_G_T_A_C_G_A_Chol |
| SEQ ID NO: 49 | T_C_G_A_A_T_T_C_G_A_Chol |
| SEQ ID NO: 50 | T_C_G_T_T_A_A_C_G_A_Chol |
| SEQ ID NO: 51 | T_C_G_A_A_C_G_T_T_C_G_A_Chol |
| SEQ ID NO: 52 | T_C_G_T_T_C_G_A_A_C_G_A_Chol |
| SEQ ID NO: 53 | T_C_G_A_C_G_A_T_C_G_T_C_G_A_Chol |
| SEQ ID NO: 54 | T_C_G_G_A_C_G_A_T_C_G_T_C_C_G_A_Chol |
| SEQ ID NO: 55 | T_C_G_A_C_G_A_G_C_T_C_G_T_C_G_A_Chol |
| SEQ ID NO: 56 | T_C_G_G_C_G_G_C_C_G_C_C_G_A_Chol |
| SEQ ID NO: 57 | T_C_G_A_C_G_T_C_G_A*Chol |
| SEQ ID NO: 58 | T_C_G_A_C_G_T_C_**G*A**_Chol |
| SEQ ID NO: 59 | T_C_G_A_C_G_T_**C*G*A**_Chol |
| SEQ ID NO: 60 | T_C_G_A_C_G_**T*C*G*A**_Chol |
| SEQ ID NO: 61 | G_C_G_A_C_G_T_C_G_A_Chol |
| SEQ ID NO: 62 | C_C_G_A_C_G_T_C_G_A_Chol |
| SEQ ID NO: 63 | I_C_G_A_C_G_T_C_G_A_Chol |
| SEQ ID NO: 64 | U_C_G_A_C_G_T_C_G_A_Chol |
| SEQ ID NO: 65 | Z_C_G_A_C_G_T_C_G_A_Chol |
| SEQ ID NO: 66 | T_T_C_G_A_C_G_T_C_G_A_Chol |
| SEQ ID NO: 67 | T_T_T_C_G_A_C_G_T_C_G_A_Chol |
| SEQ ID NO: 68 | T_C_G_T_C_G_A_C_G_T_C_G_A_Chol |
| SEQ ID NO: 69 | T_C_G_A_A_T_A_T_A_T_T_A_C_G_A_chol |
| SEQ ID NO: 70 | T_C_G_A_A_T_A_T_A_T_T_A_chol |
| SEQ ID NO: 71 | T_C_A_T_C_G_A_T_G_A_Chol |
| SEQ ID NO: 72 | T_C_G_A_C_G_T_T_G_A_Chol |

TABLE 1-continued

| ODN # | Sequence |
|---|---|
| SEQ ID NO: 73 | F_C_G_A_C_G_F_C_G_A_Chol |
| SEQ ID NO: 74 | T_H_G_A_H_G_T_H_G_A_Chol |
| SEQ ID NO: 75 | T_Z_G_A_Z_G_T_Z_G_A_Chol |
| SEQ ID NO: 76 | T_C_G_V_C_G_T_C_G_V_Chol |
| SEQ ID NO: 77 | T_C_V_A_C_V_T_C_V_A_Chol |
| SEQ ID NO: 78 | T_C_R_A_C_R_T_C_R_A_Chol |
| SEQ ID NO: 79 | T_C_O_A_C_O_T_C_O_A_Chol |
| SEQ ID NO: 80 | T_C_S_A_C_S_T_C_S_A_Chol |
| SEQ ID NO: 81 | T_C_G_S_C_G_T_C_G_S_Chol |
| SEQ ID NO: 82 | T_S_G_A_S_G_T_S_G_A_Chol |
| SEQ ID NO: 83 | T_C_G_A_C_G_S_C_G_A_Chol |
| SEQ ID NO: 84 | T_C_6G_A_C_6G_T_C_6G_A_Chol |
| SEQ ID NO: 85 | ff_C_G_A_C_G_T_C_G_A_Chol |
| SEQ ID NO: 86 | 4T_C_G_A_C_G_T_C_G_A_Chol |
| SEQ ID NO: 87 | yU_C_G_A_C_G_T_C_G_A_Chol |
| SEQ ID NO: 88 | 5U_C_G_A_C_G_T_C_G_A_Chol |
| SEQ ID NO: 89 | T_C_D_A_C_G_T_C_G_A_Chol |
| SEQ ID NO: 90 | T_C_G_A_D_G_T_C_G_A_Chol |
| SEQ ID NO: 91 | T_C_G_A_C_G_T_C_D_A_Chol |
| SEQ ID NO: 92 | T_C_G_A_D_D_T_C_G_A_Chol |
| SEQ ID NO: 93 | 5T_C_G_A_C_G_T_C_G_A_Chol |
| SEQ ID NO: 94 | 3T_C_G_A_C_G_T_C_G_A_Chol |
| SEQ ID NO: 95 | T_aC_G_A_aC_G_T_aC_G_A_Chol |
| SEQ ID NO: 96 | T_fC_G_A_fC_G_T_fC_G_A_Chol |
| SEQ ID NO: 97 | fU_C_G_A_C_G_fU_C_G_A_Chol |
| SEQ ID NO: 98 | mU_C_G_A_C_G_T_C_G_A_Chol |
| SEQ ID NO: 99 | mU_mC_mG_mA_mC_mG_mU_mC_mG_mA_Chol |
| SEQ ID NO: 100 | rU_C_G_A_C_G_T_C_G_A_Chol |
| SEQ ID NO: 101 | rU_rC_rG_rA_rC_rG_rU_rC_rG_rA_Chol |
| SEQ ID NO: 102 | mU&mC&mG&mA&mC&mG&mU&mC&mG&mA_Chol |
| SEQ ID NO: 103 | T_C_G_A_C_G_T_C_G_A_D_D_D_D_T_C_G_A_C_G_T_C_G_A_chol |
| SEQ ID NO: 104 | 3'-teg_A_G_C_T_G_C_A_G_C_T_(5'5'link)D_D_D_D_T_C_G_A_C_G_T_C_G_A_chol-3' |

The symbol * refers to the presence of a stabilized internucleotide linkage and _: refers to the presence of a phosphodiester linkage. The following are definitions of symbols and letters in table 1:
& 2'5'-linkage as phosphodiester
* phosphorothioate
*p 5'-Thiophosphate
_ phosphodiester (PO-bonds)
A, C, G, T 2'-Deoxynucleotide (dA, dC, dG, T)
chol Cholesterol
D dSpacer (abasic residue)
7 7-Deaza-dG
F 5-Fluoro-dU
H 5-Hydroxy-dC
I Inosine (deoxy)
J Spacer C3 (propanediol phosphate)
L Spacer 18 (hexaethylenglycol phosphate)
mA, mC, mG 2'-oder 3'-O-Methyl Ribonucleotide (A, C, G)
mA, mC, mG 3'-O-Methyl-A (C, G)
mT 3'-O-Methyl-T
mU 2'-O-Methyl Uridine
O 8-Oxo-dG
p* 3'-Thiophosphate
Q 8-Oxo-dA
R 2-Aminopurine (deoxyribofuranoside)
rA, rC, rG, rU RNA
S 5NI = 5-Nitroindol
teg Spacer 9 (triethylenglycol phosphate)
U 2'-Deoxyuridine
V 2.6-Diaminopurine (deoxyribofuranoside)
vitE Vitamin E
W Nebularine (deoxyribofuranoside)
Z 5-Methyl-deoxycytidine
5T 5-Methoxy-deoxythymidine
doub Doubler (Glenresearch)
doub2 Doubler2 (Chemgenes)
but 1,4-Butandiole
6G 6-Thiodeoxyguanosine
ff Difluorotoluyldeoxyribonucleotide
4T 4-Thiothymidine
yU Pseudodeoxyuridine
5U 5-Hydroxymethyldeoxyuridine
5T 5-Methoxythymidine
3T 2'3'-Dideoxythymidine
aC Ara-cytidine (5'5'-linked)
fC 2'-Fluoro-cytidine
fU 2'-Fluoro-uridine
rU Ribo-uridine
bC 5'-Bromo-cytidine
eC N-4-Ethyl-cytidine
dP P-Base
cC Amino-Modifier-C6-cytidine The invention also relates to compositions that are a set of oligonucleotides forming a duplex. As shown in the examples below, the oligonucleotides have minimal or no activity when used alone. However when they are prepared as a duplex the activity of the duplex is greatly enhanced.

The duplex that forms between the two oligonucleotides has partial complementarity. Partial complementarity refers to at least a portion of the duplex that includes nucleotides that base-pair with one another. Thus one region of the first oligonucleotide may include at least some nucleotides that form a base pair with complementary nucleotides in a region of the second oligonucleotide. The partial complementarity is that amount that is sufficient to stabilize the duplex in the presence or absence of an exogenous stabilizer. In general the region of partial complementarity should include at least 2 nucleotides on each oligonucleotide that are capable of base pairing with the other oligonucleotide, depending on the length of the oligonucleotide pair. In some embodiments it is preferred that the region of partial complementarity is greater than 2 nucleotides. For instance it may include at least 3, 4, 5, 6, 7, 8, 9, or 10 nucleotides on each oligonucleotide. Thus, the region of the nucleotides that has partial complementarity may include one or more nucleotide mis-matches.

Alternatively the entire region of the nucleotide participating in the duplex may be perfectly complementary. A region that is perfectly complementary is one that includes only nucleotides that base-pair with a complementary nucleotide on the other oligonucleotide.

The duplex can be stabilized by the interaction between the base-pairing nucleotides. In some instances, the duplex may be stabilized or further stabilized with the use of an exogenous stabilizer. An exogenous stabilizer is any molecule, such as a linker that reduces the level of disassociation of the duplex, or in other words increases the stability of the duplex.

At least one of the oligonucleotides includes a YR motif and preferably a CG motif. One or both oligonucleotides may include a palindrome, but it is not necessary. In some embodiments neither oligonucleotide includes a palindrome.

An example of a functionally active duplex of oligonucleotides is SEQ ID NO: 108 and SEQ ID NO: 109.

```
SEQ ID NO: 108    5'-T_C_G_T_C_G_T_C_G_A_Chol
SEQ ID NO: 109    Chol-A_G_C_A_G_C_A_G_C_T-5'
```

It has been discovered according to the invention that the subsets of lipophilic conjugates have dramatic immune stimulatory effects on human cells, suggesting that these conjugates are effective therapeutic agents for human vaccination, cancer immunotherapy, asthma immunotherapy, general enhancement of immune function, enhancement of hematopoietic recovery following radiation or chemotherapy, and other immune modulatory applications.

As used herein, the terms treat, treated, or treating when used with respect to a disorder such as an infectious disease, cancer, allergy, or asthma refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

Thus the Lipophilic conjugates are useful in some aspects of the invention as a vaccine for the treatment of a subject having or at risk of developing allergy or asthma, an infection with an infectious organism or a cancer in which a specific cancer antigen has been identified. The Lipophilic conjugates can also be given alone without the antigen or allergen for protection against infection, allergy or cancer or may be administered with other therapeutic agents. Repeated doses may allow longer term protection. A subject at risk as used herein is a subject who has any risk of exposure to an infection causing pathogen or a cancer or an allergen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or directly to the organism or even any subject living in an area where an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject may be exposed to the antigen, i.e., during pollen season, then that subject is at risk of exposure to the antigen. A subject at risk of developing an allergy to asthma includes those subjects that have been identified as having an allergy or asthma but that don't have the active disease during the Lipophilic conjugate treatment as well as subjects that are considered to be at risk of developing these diseases because of genetic or environmental factors.

A subject at risk of developing a cancer is one who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with a Lipophilic conjugate and optionally an antigen specific for the type of cancer to which the subject is at risk of developing, the subject may be able to kill the cancer cells as they develop. If a tumor begins to form in the subject, the subject will develop an innate immune response or a specific immune response against the tumor antigen.

In addition to the use of the Lipophilic conjugates for prophylactic treatment, the invention also encompasses the use of the Lipophilic conjugates for the treatment of a subject having an infection, an allergy, asthma, or a cancer.

A subject having an infection is a subject that has been exposed to an infectious pathogen and has acute or chronic detectable levels of the pathogen in the body. The Lipophilic conjugates can be used with or without an antigen or other therapeutic to mount an innate or an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

A subject having an allergy is a subject that is capable of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, allergic asthma, urticaria (hives) and food allergies, and other atopic conditions.

Allergies are generally caused by IgE antibody generation against harmless allergens. The cytokines that are induced by systemic or mucosal administration of Lipophilic conjugates are predominantly of a class called Th1 (examples are IL-12, IP-10, IFN-α and IFN-γ) and these induce both humoral and cellular immune responses. The other major type of immune response, which is associated with the production of IL-4 and IL-5 cytokines, is termed a Th2 immune response. In general, it appears that allergic diseases are mediated by Th2 type immune responses. Based on the ability of the Lipophilic conjugates described herein to shift the immune response in a subject from a predominant Th2 (which is associated with production of IgE antibodies and allergy) to a balanced Th2/Th1 response (which is protective against allergic reactions), an effective dose for inducing an immune response of a Lipophilic conjugate can be administered to a subject to treat asthma and allergy.

Thus, the Lipophilic conjugates have significant therapeutic utility in the treatment of allergic conditions and asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. Asthma refers to a disorder of the respiratory system characterized by inflammation, narrowing of the airways and increased reactivity of the airways to inhaled agents. Asthma is frequently, although not exclusively associated with atopic or allergic symptoms. Thus, asthma includes allergic asthma and non-allergic asthma.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

A subject shall mean a human or vertebrate animal or mammal including but not limited to a dog, cat, horse, cow, pig, sheep, goat, turkey, chicken, primate, e.g., monkey, and fish (aquaculture species), e.g. salmon. Thus, the compounds may be used to treat cancer and tumors, infections, and allergy/asthma in human and non human subjects. Cancer is one of the leading causes of death in companion animals (i.e., cats and dogs).

In the instances when the CpG oligonucleotide is administered with an antigen, the subject may be exposed to the antigen. As used herein, the term exposed to refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the Lipophilic conjugate are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the Lipophilic conjugate. For instance, in a subject at risk of developing a cancer or an infectious disease or an allergic or asthmatic response, the subject may be administered the Lipophilic conjugate on a regular basis when that risk is greatest, i.e., during allergy season or after exposure to a cancer causing agent. Additionally the Lipophilic conjugate may be administered to travelers before they travel to foreign lands where they are at risk of exposure to infectious agents. Likewise the Lipophilic conjugate may be administered to soldiers or civilians at risk of exposure to biowarfare to induce a systemic or mucosal immune response to the antigen when and if the subject is exposed to it.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and multicellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research,* 54:1055, by partially purifying the antigens, by recombinant technology, or by de novo synthesis of known antigens. Cancer antigens include but are not limited to antigens that are recombinantly expressed, an immunogenic portion thereof, or a whole tumor or cancer cell. Such antigens can be isolated or prepared recombinantly or by any other means known in the art.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of viruses that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papoaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), Hepatitis C; Norwalk and related viruses, and astroviruses).

Both gram negative and gram positive bacteria serve as antigens in vertebrate animals. Such gram positive bacteria include, but are not limited to, *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus (anaerobic sps.), Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israeli*.

Examples of fungi include *Cryptococcus neoformans, Histoplasma capsulatum, Coccidioides immitis, Blastomyces dermatitidis, Chlamydia trachomatis, Candida albicans*.

Other infectious organisms (i.e., protists) include *Plasmodium* spp. such as *Plasmodium falciparum, Plasmodium malariae, Plasmodium ovale*, and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Other medically relevant microorganisms have been described extensively in the literature, e.g., see C. G. A Thomas, *Medical Microbiology*, Bailliere Tindall, Great Britain 1983, the entire contents of which is hereby incorporated by reference.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: *Canine (Canis familiaris); Dermatophagoides (e.g. Dermatophagoides farinae); Felis (Felis domesticus); Ambrosia (Ambrosia artemiisfolia; Lolium (e.g. Lolium perenne or Lolium multiflorum); Cryptomeria (Cryptomeria japonica); Alternaria (Alternaria alternata); Alder; Alnus (Alnus gultinoasa); Betula (Betula verrucosa); Quercus (Quercus alba); Olea (Olea europa); Artemisia (Artemisia vulgaris); Plantago (e.g. Plantago lanceolata); Parietaria (e.g. Parietaria officinalis or Parietaria judaica); Blattella (e.g. Blattella germanica); Apis (e.g. Apis multiflorum);  Cupressus (e.g. Cupressus sempervirens, Cupressus arizonica and Cupressus macrocarpa); Juniperus (e.g. Juniperus sabinoides, Juniperus virginiana, Juniperus communis and Juniperus ashei); Thuya (e.g. Thuya orientalis); Chamaecyparis (e.g. Chamaecyparis obtusa); Periplaneta (e.g. Periplaneta americana); Agropyron (e.g. Agropyron repens); Secale (e.g. Secale cereale); Triticum (e.g. Triticum aestivum); Dactylis (e.g. Dactylis glomerata); Festuca (e.g. Festuca elatior); Poa (e.g. Poapratensis or Poa compressa); Avena (e.g. Avena sativa); Holcus (e.g. Holcus lanatus); Anthoxanthum (e.g. Anthoxanthum odoratum); Arrhenatherum (e.g. Arrhenatherum elatius); Agrostis (e.g. Agrostis alba); Phleum (e.g. Phleum pratense); Phalaris (e.g. Phalaris arundinacea); Paspalum (e.g. Paspalum notatum); Sorghum (e.g. Sorghum halepensis); and Bromus (e.g. Bromus inermis)*.

The antigen may be substantially purified. The term substantially purified as used herein refers to an antigen, i.e., a polypeptide which is substantially free of other proteins, lipids, carbohydrates or other materials with which it is naturally associated. One skilled in the art can purify polypeptide antigens using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the polypeptide antigen may also be determined by amino-terminal amino acid sequence analysis. Other types of antigens such as polysaccharides, small molecule, mimics etc are included within the invention and may optionally be substantially pure.

The conjugates of the invention may be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasitic agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocortlcoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleoside analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate form which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. $\alpha$ and $\beta$-interferon also induce the expression of Class I and Class II MHC molecules on the surface of infected cells, resulting in increased antigen presentation for host immune cell recognition. $\alpha$ and $\beta$-interferons are available as recombinant forms and have been used for the treatment of chronic hepatitis B and C infection. At the dosages which are effective for anti-viral therapy, interferons have severe side effects such as fever, malaise and weight loss.

Anti-viral agents useful in the invention include but are not limited to immunoglobulins, amantadine, interferons, nucleoside analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

Lipophilic conjugates can be combined with other therapeutic agents such as adjuvants to enhance immune responses. The Lipophilic conjugate and other therapeutic agent may be administered simultaneously or sequentially. When the other therapeutic agents are administered simultaneously they can be administered in the same or separate formulations, but are administered at the same time. The other therapeutic agents are administered sequentially with one another and with Lipophilic conjugate, when the administration of the other therapeutic agents and the Lipophilic conjugate is temporally separated. The separation in time between the administration of these compounds may be a matter of minutes or it may be longer. Other therapeutic agents include but are not limited to adjuvants, cytokines, antibodies, antigens, etc.

The compositions of the invention may also be administered with non-nucleic acid adjuvants. A non-nucleic acid adjuvant is any molecule or compound except for the Lipophilic conjugates described herein which can stimulate the humoral and/or cellular immune response. Non-nucleic acid adjuvants include, for instance, adjuvants that create a depo effect, immune stimulating adjuvants, and adjuvants that create a depo effect and stimulate the immune system.

The Lipophilic conjugates are also useful as mucosal adjuvants. It has previously been discovered that both systemic and mucosal immunity are induced by mucosal delivery of CpG nucleic acids. Thus, the oligonucleotides may be administered in combination with other mucosal adjuvants.

Immune responses can also be induced or augmented by the co-administration or co-linear expression of cytokines (Bueler & Mulligan, 1996; Chow et al., 1997; Geissler et al., 1997; Iwasaki et al., 1997; Kim et al., 1997) or co-stimulatory molecules such as B7 (Iwasaki et al., 1997; Tsuji et al., 1997) with the Lipophilic conjugates. The term cytokine is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IP-10, IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (IFN-γ), IFN-α, tumor necrosis factor (TNF), TGF-β, FLT-3 ligand, and CD40 ligand. In addition to cytokines the CpG oligonucleotides may be used in combination with antibodies against certain cytokines, such as anti-IL-10 and anti-TGF-β, as well as Cox inhibitors, i.e. COX-1 and COX-2 inhibitors.

The oligonucleotides are also useful in mediating immune responses through cellular toll-like receptors (TLRs). TLRs are a series of signaling pattern-recognition receptors known as play a major role in the inflammatory responses and the induction of immunity. Different TLRs directly or indirectly bind different microbial molecules. For example, TLR-2 recognizes peptidoglycan and lipoproteins; TLR-4 recognizes lipopolysaccharide and lipoteichoic acid; TLR-5 recognizes bacterial flagellin; and TLR-9 recognizes bacterial DNA. The stimulation of TLR transmits a signal to the cell's nucleus inducting the expression of genes coding for the synthesis of intracellular regulatory molecules such as cytokines. The cytokines, in turn, bind to cytokine receptors on other defense cells. These cytokines trigger innate immune defenses such as inflammation, fever, and phagocytosis and provide an immediate response against the invading microorganism. TLRs also participate in adoptive immunity by triggering various secondary signals needed for humoral immunity (the production of antibodies) and cell-mediated immunity (the production of cytotoxic T-lymphocytes and additional cytokines). The oligonucleotides of the invention are useful in mediating TLR immune responses, and can the oligonucleotides of the invention can stimulate the production of certain cytokines in a TLR dependent manner.

The oligonucleotides are also useful for redirecting an immune response from a Th2 immune response to a Th1 immune response. This results in the production of a relatively balanced Th1/Th2 environment. Redirection of an immune response from a Th2 to a Th1 immune response can be assessed by measuring the levels of cytokines produced in response to the nucleic acid (e.g., by inducing monocytic cells and other cells to produce Th1 cytokines, including IL-12, IFN-γ and GM-CSF). The redirection or rebalance of the immune response from a Th2 to a Th1 response is particularly useful for the treatment of asthma. For instance, an effective amount for treating asthma can be that amount; useful for redirecting a Th2 type of immune response that is associated with asthma to a Th1 type of response or a balanced Th1/Th2 environment. Th2 cytokines, especially IL-4 and IL-5 are elevated in the airways of asthmatic subjects. The Lipophilic conjugates described herein cause an increase in Th1 cytokines which helps to rebalance the immune system, preventing or reducing the adverse effects associated with a predominately Th2 immune response.

The Lipophilic conjugates have the unique capability to promote cell survival, differentiation, activation and maturation of dendritic cells, and are useful for in vitro, in vivo, and ex vivo methods involving dendritic cells.

Lipophilic conjugates also increase natural killer cell lytic activity and antibody dependent cellular cytotoxicity (ADCC). ADCC can be performed using a Lipophilic conjugate in combination with an antibody specific for a cellular target, such as a cancer cell. When the Lipophilic conjugate is administered to a subject in conjunction with the antibody the subject's immune system is induced to kill the tumor cell. The antibodies useful in the ADCC procedure include antibodies which interact with a cell in the body. Many such antibodies specific for cellular targets have been described in the art and many are commercially available.

The Lipophilic conjugates may also be administered in conjunction with an anti-cancer therapy. Anti-cancer therapies include cancer medicaments, radiation and surgical procedures. As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

Additionally, the methods of the invention are intended to embrace the use of more than one cancer medicament along with the Lipophilic conjugates. As an example, where appropriate, the Lipophilic conjugates may be administered with both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

The chemotherapeutic agent may be, for instance, methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, HYCAMTIN®/Topotecan, PKC412, Valspodar/PSC833, NOVATRONE®/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/ OK-432, AD 32/Valrubicin, Metastron/strontium derivative, TEMODAL®/Temozolomide, EVACET™/liposomal doxorubicin, Yewtaxan/Paclitaxel, TAXOL®/Paclitaxel, Xeload/ Capecitabine, FURTULON®/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/ Uracil), ERGAMISOL®/Levamisole, Eniluracil/776C85/ 5FU enhancer, Campto/Levamisole, CAMPTOSAR®/ Irinotecan, TUMODEX®/Ralitrexed, LEUSTATIN®/ Cladribine, Paxex/Paclitaxel, DOXIL®/liposomal doxorubicin, CAELYX®/liposomal doxorubicin, FLUDARA®/Fludarabine, PHARMARUBICIN®/Epirubicin, DepoCyt, ZD1839, LU 79553/Bis-Naphtalimide, LU 103793/Dolastain, Caetyx/liposomal doxorubicin, Gemzar/ Gemcitabine, ZD 0473/Anormed, YM 116, Iodine seeds, CDK4 and CDK2 inhibitors, PARP inhibitors, D4809/Dexifosamide, Ifes/Mesnex/Ifosamide, VUMON®/Teniposide, Paraplatin/Carboplatin, Plantinol/cisplatin, Vepeside/Etoposide, ZD 9331, TAXOTERE®/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Errthropoietin, Hexamethylmelamine (HMM), Interleukin 2, Mitoguazone (methyl-GAG; methyl glyoxal bis guanylhydrazone; MGBG), Pentostatin (2'deoxycoformycin), Semustine (methyl-CCNU), Teniposide (VM-26) or Vindesine sulfate, but it is not so limited.

The immunotherapeutic agent may be, for instance, Ributaxin, HERCEPTIN®, QUADRMET®, Panorex, IDEC-Y2B8, BEC2, C225, ONCOLYM®, SMART™ M195, ATRAGEN®, OVAREX®, BEXXAR®, LDP-03, ior t6, MDX-210, MDX-11, MDX-22, OV103, 3622W94, anti-VEGF, ZENAPAX®, MDX-220, MDX-447, MELIMMUNE-2, MELIMMUNE-1, CEACIDE®, PRETARGET®, NovoMAb-G2, TNT, Gliomab-H, GNI-250, EMD-72000, LYMPHOCIDE®, CMA 676, Monopharm-C, 4B5, ior egf.r3, ior c5, BABS, anti-FLK-2, MDX-260, ANA Ab, SMART 1D10 Ab, SMART ABL 364 Ab or ImmuRAIT-CEA, but it is not so limited.

The cancer vaccine may be, for instance, EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vacine, TA-HPV, TA-CIN, DISC-virus or ImmuCyst/TheraCys, but it is not so limited.

The use of Lipophilic conjugates in conjunction with immunotherapeutic agents such as monoclonal antibodies is able to increase long-term survival through a number of mechanisms including significant enhancement of ADCC (as discussed above), activation of natural killer (NK) cells and an increase in IFN-α levels. The nucleic acids when used in combination with monoclonal antibodies serve to reduce the dose of the antibody required to achieve a biological result.

The invention also includes methods for inducing antigen non-specific innate immune activation and broad spectrum resistance to infectious challenge using the Lipophilic conjugates. The term innate immune activation as used herein refers to the activation of immune cells other than memory B cells and for instance can include the activation of NK cells, T cells and/or other immune cells that can respond in an antigen independent fashion. A broad spectrum resistance to infectious challenge is induced because the immune cells are in active form and are primed to respond to any invading compound or microorganism. The cells do not have to be specifically primed against a particular antigen. This is particularly useful in biowarfare, and the other circumstances described above such as travelers.

The conjugates of the invention may be formulated as other oligonucleotides, or with variations due to the lipophilic group, e.g., the formation of multimers by the binding or embedding of the L group in a surface, such as a liposome, ISCOM, or other suitable hydrophobic bead or formulation. The conjugates may be formulated in a complex with a desired carrier structure, such as a polymer, a peptide, a protein, or a nucleic acid of interest. The conjugates may be formulated in vesicles comprising mainly or almost exclusively a lipophilic compound as described herein. The present invention also provides a method for increasing the lipophilicity of an immunostimulatory oligonucleotide in order to increase its affinity to a formulation reagent. Therefore, the oligonucleotides described herein posses favorable properties when encapsulated in a lipid composition. In conventional liposomes, it is often difficult to entrap a high concentration of a drug. By lipophilic derivatisation of the immunostimulatory oligonucleotide and incorporation into liposomes, the oligonucleotide may be more appropriate for long-term storage, since there will be less leakage of drug from the liposome. The lipophilic ligand may also lead to improved bioavailability and favorable biodistribution to certain organs, such as liver, and may also reduce toxic side effects. Without being bound to any particular mechanism of action. The free 5' ends of the ODN protruding from such multimeric macromolecules will be available to interact with the TLR9 receptor in such a way that leads to the crosslinking of the receptor, which may induce even further increased production of IFN-α.

The Lipophilic conjugate and/or the antigen and/or other therapeutics may be administered alone (e.g., in saline or buffer) or using any delivery vehicles known in the art. For instance the following delivery vehicles have been described: Cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); Liposomes (Childers et al., 1999, Michalek et al., 1989, 1992, de Haan 1995a, 1995b); Live bacterial vectors (e.g., *Salmonella, Escherichia coli, Bacillus calmatte-guerin, Shigella, Lactobacillus*) (Hone et al., 1996, Pouwels et al., 1998, Chatfield et al., 1993, Stover et al., 1991, Nugent et al., 1998); Live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); Microspheres (Gupta et al., 1998, Jones et al., 1996, Maloy et al., 1994, Moore et al., 1995, O'Hagan et al., 1994, Eldridge et al., 1989); Nucleic acid vaccines (Fynan et al., 1993, Kuklin et al., 1997, Sasaki et al., 1998, Okada et al., 1997, Ishii et al., 1997); Polymers (e.g. carboxymethylcellulose, chitosan) (Hamajima et al., 1998, Jabbal-Gill et al., 1998); Polymer rings (Wyatt et al., 1998); Proteosomes (Vancott et al., 1998, Lowell et al., 1988, 1996, 1997); Sodium Fluoride (Hashi et al., 1998); Transgenic plants (Tacket et al., 1998, Mason et al., 1998, Haq et al., 1995); Virosomes (Gluck et al., 1992, Mengiardi et al., 1995, Cryz et al., 1998); Virus-like particles (Jiang et al., 1999, Leibl et al., 1998). Other delivery vehicles are known in the art.

The term effective amount of a Lipophilic conjugate refers to the amount necessary or sufficient to realize a desired biologic effect. For example, an effective amount of a Lipophilic conjugate administered with an antigen for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular Lipophilic conjugate being administered the size of the subject, or the severity of the disease or condition. One of ordinary skill in the art can empirically determine the effective amount of a particular Lipophilic conjugate and/or antigen and/or other therapeutic agent without necessitating undue experimentation.

Subject doses of the compounds described herein for mucosal or local delivery typically range from about 10 µg to 1000 mg per administration, which depending on the application could be given daily, weekly, or monthly and any other amount of time therebetween or as otherwise required. More typically mucosal or local doses range from about 100 µg to 50 mg per administration, and most typically from about 500 µg to 5 mg, with 2-4 administrations being spaced days or weeks apart. More typically, immune stimulant doses range from 100 µg to 1000 mg per administration, and most typically 500 µg to 50 mg, with daily or weekly administrations. Doses of the compounds described herein for parenteral delivery for the purpose of inducing an innate immune response or for increasing ADCC or for inducing an antigen specific immune response when the Lipophilic conjugates are administered in combination with other therapeutic agents or in specialized delivery vehicles typically range from about 10 µg to 1000 mg per administration, which depending on the application could be given daily, weekly, or monthly and any other amount of time therebetween or as otherwise required. More typically parenteral doses for these purposes range from about 100 µg to 50 mg per administration, and most typically from about 1000 µg to 10 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for other CpG oligonucleotides which have been tested in humans (human clinical trials are ongoing) and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the Lipophilic conjugate an/or other therapeutics can be administered to a subject by any mode that delivers the compound to the desired surface, e.g., local, mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, and rectal.

For oral administration, the compounds (i.e., Lipophilic conjugates, antigens and/or other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

The compounds may be administered by inhalation to pulmonary tract, especially the bronchi and more particularly into the alveoli of the deep lung, using standard inhalation devices. The compounds may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. An inhalation apparatus may be used to deliver the compounds to a subject. An inhalation apparatus, as used herein, is any device for administering an aerosol, such as dry powdered form of the compounds. This type of equipment is well known in the art and has been described in detail, such as that description found in Remington: The Science and Practice of Pharmacy, 19$^{th}$ Edition, 1995, Mac Publishing Company, Easton, Pa., pages 1676-1692. Many U.S. patents also describe inhalation devices, such as U.S. Pat. No. 6,116,237.

"Powder" as used herein refers to a composition that consists of finely dispersed solid particles. Preferably the compounds are relatively free flowing and capable of being dispersed in an inhalation device and subsequently inhaled by a subject so that the compounds reach the lungs to permit penetration into the alveoli. A "dry powder" refers to a powder composition that has a moisture content such that the particles are readily dispersible in an inhalation device to form an aerosol. The moisture content is generally below about 10% by weight (% w) water, and in some embodiments is below about 5% w and preferably less than about 3% w. The powder may be formulated with polymers or optionally may be formulated with other materials such as liposomes, albumin and/or other carriers.

Aerosol dosage and delivery systems may be selected for a particular therapeutic application by one of skill in the art, such as described, for example in Gonda, I. "Aerosols for delivery of therapeutic and diagnostic agents to the respiratory tract," in Critical Reviews in Therapeutic Drug Carrier Systems, 6:273-313 (1990), and in Moren, "Aerosol dosage forms and formulations," in Aerosols in Medicine. Principles, Diagnosis and Therapy, Moren, et al., Eds., Esevier, Amsterdam, 1985.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The Lipophilic conjugates and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a Lipophilic conjugate and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods Examples 1-5

Oligodeoxynucleotides. All ODN were provided by Coley Pharmaceutical Group (Langenfeld, Germany) and had undetectable endotoxin levels (<0.1 EU/ml) measured by the Limulus assay (BioWhittaker, Verviers, Belgium). ODN were suspended in sterile, endotoxin-free Tris-EDTA (Sigma, Deisenhofen, Germany), and stored and handled under aseptic conditions to prevent both microbial and endotoxin contamination. All dilutions were carried out using pyrogen-free phosphate-buffered saline (Life Technologies, Eggenstein, Germany).

TLR9 assay. HEK293 cells were transfected by electroporation with vectors expressing the human TLR9 and a 6×NFκB-luciferase reporter plasmid. Stable transfectants ($3\times10^4$ cells/well) were incubated with ODN for 16 h at 37° C. in a humidified incubator. Each data point was done in triplicate. Cells were lysed and assayed for luciferase gene activity (using the Britlite kit from Perkin-Elmer, Ueberlingen, Germany). Stimulation indices were calculated in reference to reporter gene activity of medium without addition of ODN.

Cell purification. Peripheral blood buffy coat preparations from healthy human donors were obtained from the Blood Bank of the University of Düsseldorf (Germany) and PBMC were purified by centrifugation over Ficoll-Hypaque (Sigma). Cells were cultured in a humidified incubator at 37° C. in RPMI 1640 medium supplemented with 5% (v/v) heat inactivated human AB serum (BioWhittaker) or 10% (v/v) heat inactivated FCS, 1.5 mM L-glutamine, 100 U/ml penicillin and 100 μg/ml streptomycin (all from Sigma).

Cytokine detection. PBMC were resuspended at a concentration of $5\times10^6$ cells/ml and added to 48 well flat-bottomed plates (1 m/well) or 96 well round-bottomed plates (200 μl/well), which had previously received nothing or ODN in different concentrations. Culture supernatants (SN) were collected after the indicated time points. If not used immediately, supernatants were frozen at −20° C. until required. Amounts of cytokines in the supernatants were assessed using commercially available ELISA Kits (IL-6, IL-10; from Diaclone, Besancon, France) or an in-house ELISA developed using commercially available antibodies (from PBL, New Brunswick, N.J., USA for detection of multiple IFN-α species).

Materials and Methods Examples 6-9

CpG ODN. The CpG ODN used were of sequences TCGTCGTTTTGTCGTTTTGTCGTT (SEQ ID NO: 116) and T-C-G-A-C-G-T-C-G-A-Cholesterol (SEQ ID NO: 13). The GpC analogue of SEQ ID NO: 116 was used as a non-CpG control. All ODN were supplied by Coley Pharmaceutical Group (Wellesley, Mass.). All ODN were re-suspended in sterile, endotoxin free TE at pH 8.0 (OmniPer®; EM Science, Gibbstown, N.J.) and stored and handled under aseptic conditions to prevent both microbial and endotoxin contamination. Dilution of ODNs for assays was carried out in sterile, endotoxin free PBS at pH 7.2 (Sigma Chemical Company, St. Lois, Mo.).

Animals. Female BALB/c mice (purchased from Charles River Canada; Montreal, Quebec, Canada, TLR9 knock out or their wild type counterparts (obtained from Dr. S. Akira at Osaka University, Japan and bred at the Coley Canada Animal Care Facility) all at 6-8 weeks of age were used for experiments. All animals were housed in micro-isolators at the Coley Canada Animal Care Facility and experiments were carried out with approval of the Animal Care Committee and under the guidelines of the Canadian Council on Animal Care.

In vitro assays. Naive BALB/c splenocytes ($5\times10^6$ cells per ml) were stimulated with either CPG SEQ ID NO: 116, CpG SEQ ID NO: 13 or the non-CpG control at 0.3, 1, 3 or 10 μg/ml. Concanavalin A (10 μg/ml, Sigma Chemical Company) and/or LPS (10 μg/ml, Sigma Chemical Company) were used as positive controls and cells cultured with media alone were used as negative controls. Culture supernatants were collected at 6 hr (for TNF-α) or at 24 hr (for IL-6 and IL-12) and were tested for cytokines using commercial ELISA kits (mouse OptEIA kits; PharMingen, Mississauga, ON).

In vivo assays. Female BALB/c mice (n=3 or 5/group) were injected either subcutaneously or intravenously with 500 μg of ODN or 500 μl PBS (negative control) and bled at 3 or 8 hrs post ODN administration. Plasma was tested for IP-10, IL-6 or IL-12 by ELISA.

Example 1

Lipophilic Conjugates Demonstrate Enhanced IFN-α Production

Human PBMC were incubated with increasing concentrations of SEQ ID NO: 36 (CpG B-Class), SEQ ID NO: 39 (CpG C-Class), non-CpG control, SEQ ID NO: 40 (CpG A-Class), non-CpG control A-Class or SEQ ID NO: 4 (CpG ODN with lipophilic conjugate) for 48 h. Supernatants were harvested and IFN-α measured by ELISA. Shown is the Mean±SEM of three blood donors. The results are shown in FIG. 1. The CpG ODN with lipophilic conjugate, the CpG C-Class oligonucleotide, and the CpG A-Class oligonucleotide all induced IFN-α production. The CpG ODN with lipophilic conjugate at a concentration of 0.5 μg/ml and 2 μg/ml was measured to induce IFN-α production of about 1000 pg/ml and 3250 pg/ml respectively. The CpG B-Class oligonucleotide, the non-CpG control oligonucleotide, and the non-CpG control A-Class oligonucleotide did not induce any measurable IFN-α response.

Example 2

Lipophilic Conjugates Demonstrate Potency in IL-6 Production

Human PBMC were incubated with increasing concentrations of SEQ ID NO: 36 (CpG B-Class), SEQ ID NO: 39 (CpG C-Class), non-CpG control, SEQ ID NO: 40 (CpG A-Class), non-CpG control A-Class or SEQ ID NO: 4 (CpG ODN with lipophilic conjugate) for 24 h. Supernatant were harvested and IL-6 measured by ELISA. Shown is the Mean±SEM of three blood donors. The results are shown in FIG. 2. In this assay the CpG ODN with lipophilic conjugate at a concentration of 2 μg/ml showed the highest measured induction of IL-6 in comparison to the other ODNs used, about 750 μg/ml. At lower concentrations (0.031, 0.125 and 0.5) the CpG ODN with lipophilic conjugate induced IL-6 with reduced potency. The CpG B-Class, CpG C-Class and to certain extend the CpG A-Class, ODNs all demonstrated potency in IL-6 induction. The non-CpG control and the non-CpG control A-Class oligonucleotides showed no or low capacity for induction of IL-6.

Example 3

Lipophilic Conjugates Demonstrate Reduced Potency in IL-10 Production

Human PBMC were incubated with increasing concentrations of SEQ ID NO: 36 (CpG B-Class), SEQ ID NO: 39 (CpG C-Class), non-CpG control, SEQ ID NO: 40 (CpG A-Class), non-CpG control A-Class or SEQ ID NO: 4 (CpG ODN with lipophilic conjugate) for 24 h. Supernatants were harvested and IL-6 measured by ELISA. Shown is the Mean±SEM of three blood donors. The results are shown in FIG. 3. The CpG ODN with lipophilic conjugate showed significantly reduced potency in stimulating IL-10 production. Even at the highest concentration used 2 μg/ml the CpG ODN with lipophilic conjugate did not significantly induce IL-10 stimulation. Similar results were obtained with the A-Class ODN, while in contrast the B-Class ODN and the C-Class ODN showed high capacity for induction of IL-10 production. The non-CpG control and the non-CpG control A-Class oligonucleotides showed no or low capacity for induction of IL-10.

Example 4

Lipophilic Conjugates Induce TLR9-Dependent NFκB Signaling

HEK293 cells expressing the human TLR9 were incubated with the indicated is ODN concentrations. NFκB stimulation was measured through luciferase activity. Stimulation indices were calculated in reference to luciferase activity of medium without addition of CpG ODN (fold induction of luciferase activity). The results are shown in FIG. 4. The CpG ODN with lipophilic conjugate at the highest used dose of 10 μg/ml induced a stimulation index of about 20. In comparison the B-Class ODN induced a stimulation index of 20 at a much lower concentration of 0.625 10 μg/ml. The A-Class ODN showed the lowest NFκB stimulation and the highest measured stimulation index was 5 for an ODN concentration of 10 μg/ml.

Example 5

Effect of Sequence and Lipophilic Group of Conjugate on IFN-α Production

Human PBMC of three donors were incubated for 48 h with the indicated ODN. Supernatants were harvested and IFN-α measured by ELISA. Shown is the level of activation of each ODN by –: no; +: low; +/++: intermediate; +++/++++: strong, as well as the maximal IFN-α amount induced by each ODN. The results are shown in Table 2.

TABLE 2

| ODN # | Sequence and Modification | IFN-α secretion | |
|---|---|---|---|
| SEQ ID NO: 36 | T*C*G*T*C*G*T*T*T*T* G*T*C*G*T*T*T*T*G*T* C*G*T*T | + | 65/400 |
| SEQ ID NO: 40 | G*G*G_G_A_C_G_A_C_G_ T_C_G_T_G_G*G*G*G*G | + + + + | 3134 |
| SEQ ID NO: 3 | T*C_G_A_C_G_T_C_G*T- Chol | + | 1126 |
| SEQ ID NO: 4 | T_C_G_A_C_G_T_C_G_T_ Chol | + + + | 2134 |
| SEQ ID NO: 5 | Chol-T_C_G_A_C_G_T_C_ G_T-Chol | + | 456 |
| SEQ ID NO: 6 | Chol_T_C_G_A_C_G_T_C_ G_T_teg | – | 7 |
| SEQ ID NO: 36 | T*C*G*T*C*G*T*T*T*T* G*T*C*G*T*T*T*T*G*T* C*G*T*T | + | 58 |
| SEQ ID NO: 39 | T*C*G*T*C*G*T*T*T*T* C*G*G*C*G*C*G*C*G*C* C*G | + + + | 3198 |

TABLE 2-continued

| ODN # | Sequence and Modification | IFN-α secretion | |
|---|---|---|---|
| SEQ ID NO: 40 | G*G*G_G_A_C_G_A_C_G_ T_C_G_T_G_G*G*G*G*G | + + + + | 5018 |
| SEQ ID NO: 4 | T_C_G_A_C_G_T_C_G_T_ Chol | + + + | 3439 |
| SEQ ID NO: 7 | T_C_G_T_C_G_A_C_G_T_ G_Chol | + + + | 3395 |
| SEQ ID NO: 8 | T_C_G_A_C_G_T_C_G_T_ T_Chol | + + + | 3383 |
| SEQ ID NO: 9 | G_T_C_G_A_C_G_T_C_G_ T_Chol | + + + | 3408 |
| SEQ ID NO: 10 | G_T_C_G_A_C_G_T_C_G_ T_T_Chol | + + + | 3511 |
| SEQ ID NO: 11 | T_C_G_T_C_G_A_C_G_ T_T_Chol | + + + | 3468 |
| SEQ ID NO: 19 | T_C_G_A_C_G_T_C_G_A_ C_G_T_C_G_T_Chol | + + | 3351 |
| SEQ ID NO: 25 | T*C*G*T_C_G_A_C_G_ T_C_G_T_Chol | + | 374 |
| SEQ ID NO: 26 | T*C*G*T*C*G*T*T*T*T_ C_G_A_C_G_T_C_G_T_ Chol | – | 23 |
| SEQ ID NO: 27 | T_C_G_G_C_G_G_C_C_ G_C_C_G_Chol | + + + | 3233 |
| SEQ ID NO: 28 | T*C*G*T_C_G_G_C_G_G_ C_C_G_C_C_G_T_Chol | + | 208 |
| SEQ ID NO: 29 | U_C_G_A_C_G_T_C_G_ U-Chol | + + + | 2190 |
| SEQ ID NO: 30 | T_C_I_A_C_I_T_C_I_ T-Chol | – | 9 |
| SEQ ID NO: 31 | T_C_7_A_C_7_T_C_7_ T-Chol | + + + | 2259 |
| SEQ ID NO: 36 | T*C*G*T*C*G*T*T*T*T* G*T*C*G*T*T*T*T*G*T* C*G*T*T | + | 477 |
| SEQ ID NO: 39 | T*C*G*T*C*G*T*T*T*T* C*G*G*C*G*C*G*C*G*C* C*G | + + + | 2329 |
| SEQ ID NO: 40 | G*G*G_G_A_C_G_A_C_G_ T_C_G_T_G_G*G*G*G* G | + + + + | 3667 |
| SEQ ID NO: 12 | A_C_G_A_C_G_T_C_G_ T_Chol | +/– | 71 |
| SEQ ID NO: 13 | T_C_G_A_C_G_T_C_G_ A_Chol | + + + + | 2894 |
| SEQ ID NO: 14 | G_A_C_G_A_C_G_T_C_G_ T_T_Chol | + + | 3490 |
| SEQ ID NO: 15 | T*C*G*A*C*G*T*C*G* T_Chol | – | 7 |
| SEQ ID NO: 16 | T*C_G_A_C_G_T_C_G_ T_Chol | + | 2717 |
| SEQ ID NO: 17 | T_C_G_A_C_G_T_C_ G*T_Chol | + + + | 3600 |

TABLE 2-continued

| ODN # | Sequence and Modification | IFN-α secretion | |
|---|---|---|---|
| SEQ ID NO: 18 | T_C_G_A_C_G_T_C_G_T_teg | − | 21 |
| SEQ ID NO: 19 | T_C_G_T_C_G_T_C_G_T_Chol | − | 21 |
| SEQ ID NO: 20 | T_G_C_A_G_C_T_G_C_T-Chol | − | 14 |
| SEQ ID NO: 21 | .._C_G_A_C_G_T_C_G.._Chol | − | 8 |
| SEQ ID NO: 22 | T_A_A_C_G_T_T_T_Chol | − | 24 |
| SEQ ID NO: 23 | T_G_A_C_G_T_T_T_Chol | − | 18 |
| SEQ ID NO: 32 | T_C_A_T_C_G_A_T_G_A_Chol | + | 650 |
| SEQ ID NO: 33 | ...._G_A_C_G_A_T_C_G_T_C_Chol | + | 877 |
| SEQ ID NO: 34 | T_C_A_C_C_G_G_T_G_A_Chol | − | 7 |
| SEQ ID NO: 35 | G_A_C_G_T_T_A_A_C_G_T_C_Chol | − | 0 |
| SEQ ID NO: 105 | T_C_A_A_C_G_T_T_G_A-Chol | + | 418 |
| SEQ ID NO: 36 | T*C*G*T*C*G*T*T*T*G*T*C*G*T*T*T*T*G*T*C*G*T*T | + | 315 |
| SEQ ID NO: 39 | T*C*G*T*C*G*T*T*T*C*G*G*C*G*C*G*C*G*C*C*G | + + + | 3053 |
| SEQ ID NO: 40 | G*G*G_G_A_C_G_A_C_G_T_C_G_T_G_G*G*G*G*G | + + + + | 4503 |
| SEQ ID NO: 4 | T_C_G_A_C_G_T_C_G_T_Chol | + + + | |
| SEQ ID NO: 13 | T_C_G_A_C_G_T_C_G_A_Chol | + + + + | 3610 |
| SEQ ID NO: 41 | T_C_G_A_Chol | − | 73 |
| SEQ ID NO: 42 | T_C_G_C_G_A_Chol | − | 23 |
| SEQ ID NO: 43 | T_C_G_C_G_C_G_A_Chol | − | 44 |
| SEQ ID NO: 48 | T_C_G_T_A_C_G_A_Chol | + +(+) | 2531 |
| SEQ ID NO: 44 | T_C_G_C_C_G_G_C_G_A_Chol | + + | 2060 |
| SEQ ID NO: 45 | T_C_G_G_C_G_C_C_G_A_Chol | + + + | 3654 |
| SEQ ID NO: 46 | T_C_G_C_G_C_G_C_G_A_Chol | + + + | 3573 |
| SEQ ID NO: 47 | T_C_G_T_C_G_A_C_G_A_Chol | − | 40 |
| SEQ ID NO: 49 | T_C_G_A_A_T_T_C_G_A_Chol | + + | 2788 |
| SEQ ID NO: 50 | T_C_G_T_T_A_A_C_G_A_Chol | + + + + | 4161 |
| SEQ ID NO: 51 | T_C_G_A_A_C_G_T_T_C_G_A_Chol | + +(+) | 2954 |
| SEQ ID NO: 52 | T_C_G_T_T_C_G_A_A_C_G_A_Chol | + + + + | 4033 |
| SEQ ID NO: 53 | T_C_G_A_C_G_A_T_C_G_T_C_G_A_Chol | +(+) | 3187 |
| SEQ ID NO: 56 | T_C_G_G_C_G_G_C_C_G_C_C_G_A_Chol | + | 1385 |
| SEQ ID NO: 54 | T_C_G_G_A_C_G_A_T_C_G_T_C_C_G_A_Chol | + +(+) | 3391 |
| SEQ ID NO: 36 | T*C*G*T*C*G*T*T*T*G*T*C*G*T*T*T*T*G*T*C*G*T*T | + | 776 |
| SEQ ID NO: 39 | T*C*G*T*C*G*T*T*T*C*G*G*C*G*C*G*C*G*C*C*G | + + + | 3201 |
| SEQ ID NO: 40 | G*G*G_G_A_C_G_A_C_G_T_C_G_T_G_G*G*G*G*G | + + + | 3706 |
| SEQ ID NO: 13 | T_C_G_A_C_G_T_C_G_A_Chol | + + + | 3485 |
| SEQ ID NO: 59 | T_C_G_A_C_G_T_C*G*A_Chol | + + +(+) | 2744 |
| SEQ ID NO: 60 | T_C_G_A_C_G_T*C*G*A_Chol | + + +(+) | 3297 |
| SEQ ID NO: 61 | G_C_G_A_C_G_T_C_G_A_Chol | − | 304 |
| SEQ ID NO: 62 | C_C_G_A_C_G_T_C_G_A_Chol | − | 562 |
| SEQ ID NO: 63 | I_C_G_A_C_G_T_C_G_A_Chol | − | 226 |
| SEQ ID NO: 64 | U_C_G_A_C_G_T_C_G_A_Chol | +(+) | 1578 |
| SEQ ID NO: 65 | Z_C_G_A_C_G_T_C_G_A_Chol | − | 272 |
| SEQ ID NO: 66 | T_T_C_G_A_C_G_T_C_G_A_Chol | + + +(+) | 2619 |
| SEQ ID NO: 67 | T_T_T_C_G_A_C_G_T_C_G_A_Chol | + + | 1800 |
| SEQ ID NO: 68 | T_C_G_T_C_G_A_C_G_T_C_G_A_Chol | + + + | 2593 |
| SEQ ID NO: 69 | T_C_G_A_A_T_A_T_A_T_T_A_C_G_A_chol | − | 43 |
| SEQ ID NO: 70 | T_C_G_A_A_T_A_T_A_T_T_A_chol | − | 96 |
| SEQ ID NO: 71 | T_C_A_T_C_G_A_T_G_A_Chol | − | 293 |
| SEQ ID NO: 106 | T*C*G*T*C*G*T*T*T*C_G*T*C_G*T*T_chol | − | 108 |

TABLE 2-continued

| ODN # | Sequence and Modification | IFN-α secretion | |
|---|---|---|---|
| SEQ ID NO: 107 | T_C_G_T_C_G_T_T_T_C_G_T_C_G_T_T_chol | − | 48 |
| SEQ ID NO: 36 | T*C*G*T*C*G*T*T*T*T*G*T*C*G*T*T*T*T*G*T*C*G*T*T | + | 177 |
| SEQ ID NO: 39 | T*C*G*T*C*G*T*T*T*T*C*G*G*C*G*C*G*C*G*C*C*G | + + + | 1881 |
| SEQ ID NO: 40 | G*G*G_G_A_C_G_A_C_G_T_C_G_T_G_G*G*G*G*G | + + + + | 2309 |
| SEQ ID NO: 13 | T_C_G_A_C_G_T_C_G_A_Chol | + + + | 2562 |
| SEQ ID NO: 108 | T_C_G_T_C_G_T_C_G_A_Chol | − | 35 |
| SEQ ID NO: 109 | T_C_G_A_C_G_A_C_G_A_Chol | + | 635 |
| SEQ ID NO: 108 + SEQ ID NO: 109 | | + + + | 2340 |

A palindromic or partial palindromic sequence with at least one CpG motif was required but not sufficient for high IFN-α induction. SEQ ID NO: 27 having the palindrome CGGCG-GCCGCC (SEQ ID NO: 114) and an additional T at the 5'-end resulted in potent induction of IFN-α. Addition of a G residue to the 5'-end or a T residue to the 3'-end, such as in SEQ ID NO: 9, SEQ ID NO: 10, and SEQ ID NO: 8, resulted in similar biological activity. However, significant extension of the palindrome (SEQ ID NO: 19) resulted in slightly decreased IFN-α induction. These results suggest that with an oligonucleotide of this length and design the sequence of the ODN must be at least partially palindromic and that a TCG (e.g. SEQ ID NO: 4, SEQ ID NO: 13), GTCG (SEQ ID NO: 9), GACG (SEQ ID NO: 14), or a UCG (as in SEQ ID NO: 29) motif at the 5'-end or near the 5'-end is of particular advantage to obtaining high IFN-α induction.

The 3'-cholesterol modified SEQ ID NO: 4 shows high secretion of IFN-α but low induction of IL-10 secretion, a characteristic property of A-class CpG oligonucleotides.

Example 6

In Vitro Mouse Splenocyte Stimulation

BALB/c mouse splenocytes were incubated for 24 h (FIG. 5a-b) or 6 h (FIG. 5c) with the indicated concentrations of SEQ ID NO: 13 or control SEQ ID NO: 117. SN were harvested and cytokines measured by ELISA. As shown in FIG. 5a, the CpG ODN with lipophilic conjugate induced IL-6 production in a dose dependent manner. At the highest ODN concentration tested of 10 µg/ml the measured IL-6 response was approximately 900 µg/ml. The control non-CpG ODN did not stimulate any IL-6 induction. FIG. 5b shows the induction of IL-12 by the CpG ODN with lipophilic conjugate. The CpG ODN with lipophilic conjugate induced IL-12 production in a dose dependent matter, and at the highest ODN concentration used, 10 µg/ml, the measured IL-12 induction was about 3750 µg/ml. In contrast the control non-CpG ODN did not stimulate any IL-12 production. FIG. 5c shows the induction of TNF-α by the CpG ODN with lipophilic conjugate in comparison to the control non-CpG ODN. At the concentration of 10 µg/ml, the CpG ODN with lipophilic conjugate induced about 140 µg/ml of TNF-α, while in contrast the control non-CpG ODN did not significantly induce any TNF-α production.

Example 7

In Vitro TLR9$^{+/+}$ and TLR9$^{-/-}$ Splenocyte Stimulation

Balb/c splenocytes from TLR9$^{+/+}$ (FIG. 6a) or TLR9$^{-/-}$ (FIG. 6b) mice were incubated for 24 h with the indicated concentrations of SEQ ID NO: 13 or control SEQ ID NO: 117. SN were harvested and IL-12p40 measured by ELISA. FIG. 6a shows that the CpG ODN with lipophilic conjugate induced IL-12 dose-response that was TLR-dependent. The highest concentration of CpG ODN with lipophilic conjugate used, 10 µg/ml, induced IL-12 concentration of 1200 µg/ml. In contrast, the control non-CpG ODN did not significantly induce any IL-12 production at any concentration used. FIG. 6b shows that both, the CpG ODN with lipophilic conjugate and the control non-CpG ODN did not significantly induce any IL-12 production in TLR deficient cells even at concentration of 10 µg/ml.

Example 8

In Vivo Time-Dependent Plasma IP-10 Stimulation

Balb/c mice (n=5) were injected SC with 500 µg of SEQ ID NO: 13 and bled at 1, 2, 3, 6, 8, 12 and 24 hr post ODN administration. Plasma was tested for IP-10 by ELISA (FIG. 7). As shown in FIG. 7, the CpG ODN with lipophilic conjugate stimulated production of IP-10 in time-dependent fashion. There was no detectable IP-10 induction during the first three hours post injection. At six hours post injection the IP-10 concentration was increased to 500 µg/ml. At eight hours post injection the IP-10 stimulation peaked at about 2000 µg/ml. At 12 hours post injection the IP-10 concentration decreased to about 500 µg/ml, equaling the stimulation measured at six hours post injection. At twenty-four hours post injection there was no detectable stimulation of IP-10 production. The control PBS treatment showed no induction of IP-10 production at any of the time points examined.

Example 9

In Vivo Plasma Cytokine and Chemokine Stimulation

Balb/c mice (n=3) were injected IV with 500 µg of SEQ ID NO: 13 or 500 µl PBS (negative control) and bled at 3 and 8 hrs post ODN administration. Plasma was tested for cytokines or chemokine by ELISA (FIG. 8). Solid bar=3 hr; Hatched bar=8 hr. FIG. 8a shows that the CpG ODN with lipophilic conjugate stimulated production of IP-10 in time-dependent fashion, about 9000 and 4000 µg/ml of IP-10 were stimulated at 3 and 8 hrs respectively. In contrast the control non-CPG ODN (SEQ ID NO: 117) did not stimulate any IP-10 production at the same time points. FIG. 8b shows that the stimulation of IL-12 production by the CpG ODN with lipophilic conjugate was lower at 3 hrs, about 20,000 µg/ml of IL-12, than at 8 hrs, about 25,000 µg/ml of IL-12 produced.

The control non-CpG ODN did not induce any IL-12 production at either time point tested. FIG. 8*c* shows that the CpG ODN with lipophilic conjugate stimulated production of IL-6 in time-dependent fashion. At 3 hrs post injection the IL-6 production ranged from 250 to 500 µg/ml, while at 8 hrs post injection the IL-6 production was about 400 µg/ml. The control non-CpG ODN did not show significant induction of IL-6 production in comparison to the PBS control.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. A composition comprising;

(N1PN2)·L wherein N1 and N2 are independently nucleic acids of 0-100 nucleotides in length, wherein N2 includes at least one nucleotide, P is a palindromic containing nucleic acid and comprising at least one YR dinucleotide, wherein Y is an unmethylated cytosine or a modified cytosine and R is a guanine or a modified guanine, wherein P is at least 6 nucleotides in length, and wherein L is a lipophilic group.

2. The composition of claim 1, wherein N1PN2 is 3-14 nucleotides in length.

3. The composition of claim 1, wherein L is linked to the nucleotide at the 3' end of N1PN2.

4. The composition of claim 1, wherein L is linked by a linker to a 2'-position of a nucleotide in N1PN2, to a heterocyclic base of a nucleotide in N1PN2, or a phosphodiester linkage in N1PN2.

5. The composition of claim 1, wherein L is selected from the group consisting of a cholesteryl, a modified cholesteryl, a cholesterol derivative, a reduced cholesterol, and a substituted cholesterol.

6. The composition of claim 5, wherein the reduced cholesterol is cholestan.

7. A composition comprising;

(N1PN2)·L wherein N1 and N2 are independently nucleic acids of 0-100 nucleotides in length, P is a palindromic containing nucleic acid and comprising at least two CG dinucleotides, wherein C is an unmethylated cytosine, wherein (N1PN2) is at least 6 nucleotides in length, and wherein L is a lipophilic group selected from the group consisting of bile acids, cholic acid, deoxycholate, glycolipids, phospholipids, sphingolipids, isoprenoids, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, and ibuprofen and wherein the composition includes at least two L.

8. The composition of claim 1, wherein the formula comprises N1PN2-L-N3PN4, wherein N3 and N4 are independently nucleic acids of 0-100 nucleotides in length.

9. The composition of claim 1, further comprising at least 2 L.

10. The composition of claim 1, wherein the formula comprises ([N1PN2]n-(X3)m)·(L)p wherein X3 is a linker, m is an integer from 0 to 20, n is an integer from 0 to 20, p is an integer from 1 to 10, and wherein the oligonucleotide N1PN2 has a length of 4 to 40 nucleotides.

11. The composition of claim 1, wherein the oligonucleotide includes at least one linear or branched non-nucleoside linkage.

12. The composition of claim 1, further comprising an immune stimulatory molecule associated with the composition.

13. The composition of claim 1, wherein the internucleotide linkages of the oligonucleotide are all phosphodiester linkages.

14. The composition of claim 1, wherein the oligonucleotide includes at least one stabilized internucleotide linkage.

15. The composition of claim 1, wherein at least one nucleotide in the oligonucleotide is a substituted or modified purine or pyrimidine.

16. The composition of claim 1, wherein multiple oligonucleotides are linked by multiple doubler or trebler moieties and form a dendrimer.

17. The composition of claim 1, wherein the composition includes at least one amino acid residue linked by an amide linkage.

18. The composition of claim 1, wherein the oligonucleotide includes at least one internucleotide linkage selected from the group consisting of a 3'5'-, a 2'5'-, a 3'3'- and a 5'5'-linkage.

19. The composition of claim 1, wherein the linkage between L and N1PN2—is metabolically stable.

20. The composition of claim 1, wherein the linkage between L and N1PN2—is metabolically labile.

21. The composition of claim 1, wherein L is associated with a carrier.

22. The composition of claim 1, wherein the carrier is selected from the group consisting of a liposome, ISCOM, a hydrophobic bead, a hydrophobic formulation, a polymer, a peptide, a protein, and a nucleic acid.

23. The composition of claim 1, further comprising:
a nucleic acid having at least one exposed 5' end; comprising, at least one YR dinucleotide, wherein Y is an unmethylated cytosine or a modified cytosine and R is a guanine or a modified guanine, at least one single stranded region, at least one double stranded region and wherein the nucleic acid is linked to at least one lipophilic group.

24. A composition comprising;

(N1PN2)·L wherein N1 and N2 are independently nucleic acids of 0-100 nucleotides in length, P is a palindromic containing nucleic acid and comprising at least one YR dinucleotide, wherein Y is an unmethylated cytosine or a modified cytosine and R is a guanine or a modified guanine, and wherein L is cholesterol and wherein N1 begins with 5'TCG or 5'UCG.

25. The composition of claim 24, wherein L is linked to the nucleotide at the 3' end of N1PN2.

26. The composition of claim 24, wherein N1PN2 is selected from the group consisting of 5'TCGACGTCGT3' (SEQ ID NO: 111) and 5'TCGACGTCGA3' SEQ ID NO: 112).

27. The composition of claim 10, wherein m and n are independently 1, 2, 3, 4, 5, 6, 7, 8, 9, or 10, and p is 1.

* * * * *

UNITED STATES PATENT AND TRADEMARK OFFICE
CERTIFICATE OF CORRECTION

PATENT NO. : 7,615,539 B2 Page 1 of 1
APPLICATION NO. : 10/952254
DATED : November 10, 2009
INVENTOR(S) : Uhlmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 918 days.

Signed and Sealed this

Nineteenth Day of October, 2010

David J. Kappos
*Director of the United States Patent and Trademark Office*

SEQUENCE LISTING

```
<160> NUMBER OF SEQ ID NOS: 116

<210> SEQ ID NO 1
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: triethyleneglycol phosphate
<222> LOCATION: (10)..(10)
<220> FEATURE:
<221> NAME/KEY: misc_feature
<222> LOCATION: (10)..(10)

<400> SEQUENCE: 1
tcgacgtcgt                                                          10

<210> SEQ ID NO 2
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: hexaethylenglycol phosphate
<222> LOCATION: (10)..(10)
<220> FEATURE:
<221> NAME/KEY: misc_feature
<222> LOCATION: (10)..(10)

<400> SEQUENCE: 2
tcgacgtcgt                                                          10

<210> SEQ ID NO 3
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (9)..(10)
<223> OTHER INFORMATION: phosphorothioate linkage
<220> FEATURE:
<221> NAME/KEY: misc_feature
<222> LOCATION: (10)..(10)
<223> OTHER INFORMATION: cholesterol

<400> SEQUENCE: 3
tcgacgtcgt                                                          10

<210> SEQ ID NO 4
<211> LENGTH: 10
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 4
tcgacgtcgt                                                              10

<210> SEQ ID NO 5
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: cholesterol
<220> FEATURE:
<221> NAME/KEY: misc_feature
<222> LOCATION: (10)..(10)
<223> OTHER INFORMATION: cholesterol

<400> SEQUENCE: 5
tcgacgtcgt                                                              10

<210> SEQ ID NO 6
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: cholesterol
<220> FEATURE:
<221> NAME/KEY: misc_feature
<222> LOCATION: (10)..(10)
<223> OTHER INFORMATION: triethyleneglycol phosphate

<400> SEQUENCE: 6
tcgacgtcgt                                                              10

<210> SEQ ID NO 7
<211> LENGTH: 11
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: cholesterol

<400> SEQUENCE: 7
tcgtcgacgt g                                                            11

<210> SEQ ID NO 8
<211> LENGTH: 11
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: cholesterol
```

```
<400> SEQUENCE: 8
tcgacgtcgt t                                                              11

<210> SEQ ID NO 9
<211> LENGTH: 11
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: cholesterol

<400> SEQUENCE: 9
gtcgacgtcg t                                                              11

<210> SEQ ID NO 10
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: cholesterol

<400> SEQUENCE: 10
gtcgacgtcg tt                                                             12

<210> SEQ ID NO 11
<211> LENGTH: 11
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: cholesterol

<400> SEQUENCE: 11
tcgtcgacgt t                                                              11

<210> SEQ ID NO 12
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 12
acgacgtcgt                                                                10

<210> SEQ ID NO 13
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
```

```
<223> OTHER INFORMATION: cholesterol

<400> SEQUENCE: 13
tcgacgtcga                                                              10

<210> SEQ ID NO 14
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: cholesterol

<400> SEQUENCE: 14
gacgacgtcg tt                                                           12

<210> SEQ ID NO 15
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where all linkages between bases are
      phosphorothioate linkages
<220> FEATURE:
<221> NAME/KEY: misc_feature
<222> LOCATION: (10)..(10)
<223> OTHER INFORMATION: cholesterol

<400> SEQUENCE: 15
tcgacgtcgt                                                              10

<210> SEQ ID NO 16
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: where linkage is phosphorothioate linkage
<220> FEATURE:
<221> NAME/KEY: misc_feature
<222> LOCATION: (10)..(10)
<223> OTHER INFORMATION: cholesterol

<400> SEQUENCE: 16
tcgacgtcgt                                                              10

<210> SEQ ID NO 17
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: where linkage is phosphotrohioate linkage
<220> FEATURE:
<221> NAME/KEY: misc_feature
<222> LOCATION: (10)..(10)
<223> OTHER INFORMATION: cholesterol
```

```
<400> SEQUENCE: 17
tcgacgtcgt                                                              10

<210> SEQ ID NO 18
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: triethyleneglycol phosphate

<400> SEQUENCE: 18
tcgacgtcgt                                                              10

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (16)..(16)
<223> OTHER INFORMATION: cholesterol

<400> SEQUENCE: 19
tcgacgtcga cgtcgt                                                       16

<210> SEQ ID NO 20
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 20
tcgtcgtcgt                                                              10

<210> SEQ ID NO 21
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 21
tgcagctgct                                                              10

<210> SEQ ID NO 22
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: cholesterol
```

<400> SEQUENCE: 22 cgacgtcg                                                                                       8

<210> SEQ ID NO 23
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: cholesterol

<400> SEQUENCE: 23 taacgttt                                                                                       8

<210> SEQ ID NO 24
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: cholesterol

<400> SEQUENCE: 24 tgacgttt                                                                                       8

<210> SEQ ID NO 25
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (13)..(13)
<223> OTHER INFORMATION: cholesterol

<400> SEQUENCE: 25
tcgtcgacgt cgt                                                                                13

<210> SEQ ID NO 26
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: cholesterol

<400> SEQUENCE: 26
tcgtcgtttt cgacgtcgt                                                                          19

<210> SEQ ID NO 27
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (13)..(13)

```
<223> OTHER INFORMATION: cholesterol

<400> SEQUENCE: 27
tcggcggccg ccg                                                        13

<210> SEQ ID NO 28
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (17)..(17)
<223> OTHER INFORMATION: cholesterol

<400> SEQUENCE: 28
tcgtcggcgg ccgccgt                                                    17

<210> SEQ ID NO 29
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where N is 2'-Deoxyuridine
<220> FEATURE:
<221> NAME/KEY: misc_feature
<222> LOCATION: (10)..(10)
<223> OTHER INFORMATION: cholesterol

<400> SEQUENCE: 29 ncgacgtcgt                                                            10

<210> SEQ ID NO 30
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where N is Inosine (deoxy)
<220> FEATURE:
<221> NAME/KEY: misc_feature
<222> LOCATION: (10)..(10)
<223> OTHER INFORMATION: cholesterol

<400> SEQUENCE: 30 tcnacntcnt                                                            10

<210> SEQ ID NO 31
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where N is 7-Deaza-dG
<220> FEATURE:
<221> NAME/KEY: misc_feature
<222> LOCATION: (10)..(10)
<223> OTHER INFORMATION: cholesterol

<400> SEQUENCE: 31
```

```
tcnacntcnt                                                           10
```

<210> SEQ ID NO 32
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 32

```
tcatcgatga                                                           10
```

<210> SEQ ID NO 33
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 33

```
gacgatcgtc                                                           10
```

<210> SEQ ID NO 34
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 34

```
tcaccggtga                                                           10
```

<210> SEQ ID NO 35
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: cholesterol

<400> SEQUENCE: 35

```
gacgttaacg tc                                                        12
```

<210> SEQ ID NO 36
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(24)
<223> OTHER INFORMATION: where all linkages are phosphorothioate
      linkages

```
<400> SEQUENCE: 36
tcgtcgtttt gtcgttttgt cgtt                                              24

<210> SEQ ID NO 37
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: cholesterol

<400> SEQUENCE: 37
tcgtcgtttt gtcgttttgt cgtt                                              24

<210> SEQ ID NO 38
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(24)
<223> OTHER INFORMATION: cholesterol

<400> SEQUENCE: 38
tcgtcgtttt gtcgttttgt cgtt                                              24

<210> SEQ ID NO 39
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: where all linkages are phosphorothioate
      linkages

<400> SEQUENCE: 39
tcgtcgtttt cggcgcgcgc cg                                                22

<210> SEQ ID NO 40
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 40
ggggacgacg tcgtgggggg g                                                 21

<210> SEQ ID NO 41
<211> LENGTH: 4
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: cholesterol

<400> SEQUENCE: 41
```

```
tcga                                                              4

<210> SEQ ID NO 42
<211> LENGTH: 6
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: cholesterol

<400> SEQUENCE: 42 tcgcga                                                            6

<210> SEQ ID NO 43
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: cholesterol

<400> SEQUENCE: 43 tcgcgcga                                                          8

<210> SEQ ID NO 44
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 44
tcgccggcga                                                       10

<210> SEQ ID NO 45
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 45
tcggcgccga                                                       10

<210> SEQ ID NO 46
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol
```

```
<400> SEQUENCE: 46
tctctctcta                                                          10

<210> SEQ ID NO 47
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 47
tcgtcgacga                                                          10

<210> SEQ ID NO 48
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: cholesterol

<400> SEQUENCE: 48 tcgtacga                                                             8

<210> SEQ ID NO 49
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 49
tcgaattcga                                                          10

<210> SEQ ID NO 50
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 50
tcgttaacga                                                          10

<210> SEQ ID NO 51
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: cholesterol
```

```
<400> SEQUENCE: 51
tcgaacgttc ga                                                        12

<210> SEQ ID NO 52
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: cholesterol

<400> SEQUENCE: 52
tcgttcgaac ga                                                        12

<210> SEQ ID NO 53
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (14)..(14)
<223> OTHER INFORMATION: cholesterol

<400> SEQUENCE: 53
tcgacgatcg tcga                                                      14

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (16)..(16)
<223> OTHER INFORMATION: cholesterol

<400> SEQUENCE: 54
tcggacgatc gtccga                                                    16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (16)..(16)
<223> OTHER INFORMATION: cholesterol

<400> SEQUENCE: 55
tcgacgagct cgtcga                                                    16

<210> SEQ ID NO 56
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (14)..(14)
```

<223> OTHER INFORMATION: cholesterol

<400> SEQUENCE: 56
tcggcggccg ccga                                                        14

<210> SEQ ID NO 57
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol
<220> FEATURE:
<221> NAME/KEY: misc_feature
<222> LOCATION: (10)..(10)
<223> OTHER INFORMATION: where the linkage to cholesterol is a
      phosphorothioate linkage

<400> SEQUENCE: 57
tcgacgtcga                                                             10

<210> SEQ ID NO 58
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: where the linkage is a phosphorothioate
      linkage
<220> FEATURE:
<221> NAME/KEY: misc_feature
<222> LOCATION: (10)..(10)
<223> OTHER INFORMATION: cholesterol

<400> SEQUENCE: 58
tcgacgtcga                                                             10

<210> SEQ ID NO 59
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(10)
<223> OTHER INFORMATION: where the linkages are phosphorothioate
      linkages
<220> FEATURE:
<221> NAME/KEY: misc_feature
<222> LOCATION: (10)..(10)
<223> OTHER INFORMATION: cholesterol

<400> SEQUENCE: 59
tcgacgtcga                                                             10

<210> SEQ ID NO 60
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (7)..(10)

```
<223> OTHER INFORMATION: where the linkages are phosphorothioate
      linkages
<220> FEATURE:
<221> NAME/KEY: misc_feature
<222> LOCATION: (10)..(10)
<223> OTHER INFORMATION: cholesterol

<400> SEQUENCE: 60
tcgacgtcga                                                                10

<210> SEQ ID NO 61
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 61
gcgacgtcga                                                                10

<210> SEQ ID NO 62
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 62
ccgacgtcga                                                                10

<210> SEQ ID NO 63
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where n is Inosine (deoxy)
<220> FEATURE:
<221> NAME/KEY: misc_feature
<222> LOCATION: (10)..(10)
<223> OTHER INFORMATION: cholesterol

<400> SEQUENCE: 63 ncgacgtcga                                                                10

<210> SEQ ID NO 64
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where n is 2'-Deoxyuridine
<220> FEATURE:
<221> NAME/KEY: misc_feature
<222> LOCATION: (10)..(10)
<223> OTHER INFORMATION: cholesterol
```

```
<400> SEQUENCE: 64 ncgacgtcga                                                               10

<210> SEQ ID NO 65
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where n is 5-Methyl-deoxycytidine
<220> FEATURE:
<221> NAME/KEY: misc_feature
<222> LOCATION: (10)..(10)
<223> OTHER INFORMATION: cholesterol

<400> SEQUENCE: 65 ncgacgtcga                                                               10

<210> SEQ ID NO 66
<211> LENGTH: 11
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: cholesterol

<400> SEQUENCE: 66
ttcgacgtcg a                                                             11

<210> SEQ ID NO 67
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: cholesterol

<400> SEQUENCE: 67
tttcgacgtc ga                                                            12

<210> SEQ ID NO 68
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (13)..(13)
<223> OTHER INFORMATION: cholesterol

<400> SEQUENCE: 68
tcgtcgacgt cga                                                           13

<210> SEQ ID NO 69
<211> LENGTH: 17
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: misc_feature
<222> LOCATION: (17)..(17)
<223> OTHER INFORMATION: cholesterol

<400> SEQUENCE: 69
tcgaatatat attacga                                                        17

<210> SEQ ID NO 70
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (14)..(14)
<223> OTHER INFORMATION: cholesterol

<400> SEQUENCE: 70
tcgaatatat atta                                                           14

<210> SEQ ID NO 71
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 71
tcatcgatga                                                                10

<210> SEQ ID NO 72
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 72
tcgacgttga                                                                10

<210> SEQ ID NO 73
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 5-Fluoro-dU
<220> FEATURE:
<221> NAME/KEY: misc_feature
<222> LOCATION: (10)..(10)
<223> OTHER INFORMATION: cholesterol

<400> SEQUENCE: 73 ncgacgncga                                                                10

<210> SEQ ID NO 74
```

```
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 5-Hydroxy-dC
<220> FEATURE:
<221> NAME/KEY: misc_feature
<222> LOCATION: (10)..(10)
<223> OTHER INFORMATION: cholesterol

<400> SEQUENCE: 74 tngangtnga                                                                10

<210> SEQ ID NO 75
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 5-Methyl-deoxycitidine
<220> FEATURE:
<221> NAME/KEY: misc_feature
<222> LOCATION: (10)..(10)
<223> OTHER INFORMATION: cholesterol

<400> SEQUENCE: 75 tngangtnga                                                                10

<210> SEQ ID NO 76
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 2.6-Diaminopurine
      (deoxyribofuranoside)
<220> FEATURE:
<221> NAME/KEY: misc_feature
<222> LOCATION: (10)..(10)
<223> OTHER INFORMATION: cholesterol

<400> SEQUENCE: 76 tcgncgtcgn                                                                10

<210> SEQ ID NO 77
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 2.6-Diaminopurine
      (deoxyribofuranoside)
<220> FEATURE:
<221> NAME/KEY: misc_feature
<222> LOCATION: (10)..(10)
<223> OTHER INFORMATION: cholesterol

<400> SEQUENCE: 77 tcnacntcna                                                                10
```

```
<210> SEQ ID NO 78
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 2-Aminopurine (deoxyribofuranoside)
<220> FEATURE:
<221> NAME/KEY: misc_feature
<222> LOCATION: (10)..(10)
<223> OTHER INFORMATION: cholesterol

<400> SEQUENCE: 78 tcnacntcna                                                              10

<210> SEQ ID NO 79
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 8-Oxo-dG
<220> FEATURE:
<221> NAME/KEY: misc_feature
<222> LOCATION: (10)..(10)
<223> OTHER INFORMATION: cholesterol

<400> SEQUENCE: 79 tcnacntcna                                                              10

<210> SEQ ID NO 80
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 5NI = 5-Nitroindol
<220> FEATURE:
<221> NAME/KEY: misc_feature
<222> LOCATION: (10)..(10)
<223> OTHER INFORMATION: cholesterol

<400> SEQUENCE: 80 tcnacntcna                                                              10

<210> SEQ ID NO 81
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 5NI = 5-Nitroindol
<220> FEATURE:
<221> NAME/KEY: misc_feature
<222> LOCATION: (10)..(10)
<223> OTHER INFORMATION: cholesterol

<400> SEQUENCE: 81
```
tcgncgtcgn                                                                 10

```
<210> SEQ ID NO 82
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 5NI = 5-Nitroindol
<220> FEATURE:
<221> NAME/KEY: misc_feature
<222> LOCATION: (10)..(10)
<223> OTHER INFORMATION: cholesterol

<400> SEQUENCE: 82
```
tngangtnga                                                                 10

```
<210> SEQ ID NO 83
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 5NI = 5-Nitroindol
<220> FEATURE:
<221> NAME/KEY: misc_feature
<222> LOCATION: (10)..(10)
<223> OTHER INFORMATION: cholesterol

<400> SEQUENCE: 83
```
tcgacgncga                                                                 10

```
<210> SEQ ID NO 84
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where g is 6-Thiodeoxyguanosine
<220> FEATURE:
<221> NAME/KEY: misc_feature
<222> LOCATION: (10)..(10)
<223> OTHER INFORMATION: cholesterol

<400> SEQUENCE: 84
```
tcgacgtcga                                                                 10

```
<210> SEQ ID NO 85
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where n is Difluorotoluyldeoxyribonucleotide
<220> FEATURE:
<221> NAME/KEY: misc_feature
<222> LOCATION: (10)..(10)
<223> OTHER INFORMATION: cholesterol

<400> SEQUENCE: 85
```

-continued ncgacgtcga 10

<210> SEQ ID NO 86
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where t is 4-thiothymidine
<220> FEATURE:
<221> NAME/KEY: misc_feature
<222> LOCATION: (10)..(10)
<223> OTHER INFORMATION: cholesterol

<400> SEQUENCE: 86
tcgacgtcga 10

<210> SEQ ID NO 87
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where n is Pseudodeoxyuridine
<220> FEATURE:
<221> NAME/KEY: misc_feature
<222> LOCATION: (10)..(10)
<223> OTHER INFORMATION: cholesterol

<400> SEQUENCE: 87 ncgacgtcga 10

<210> SEQ ID NO 88
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where n is 5-Hydroxymethyldeoxyuridine
<220> FEATURE:
<221> NAME/KEY: misc_feature
<222> LOCATION: (10)..(10)
<223> OTHER INFORMATION: cholesterol

<400> SEQUENCE: 88 ncgacgtcga 10

<210> SEQ ID NO 89
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: where n is dSpacer (a basic residue)
<220> FEATURE:
<221> NAME/KEY: misc_feature
<222> LOCATION: (10)..(10)
<223> OTHER INFORMATION: cholesterol

```
<400> SEQUENCE: 89 tcnacgtcga                                                                    10

<210> SEQ ID NO 90
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: where n is dSpacer (a basic residue)
<220> FEATURE:
<221> NAME/KEY: misc_feature
<222> LOCATION: (10)..(10)
<223> OTHER INFORMATION: cholesterol

<400> SEQUENCE: 90 tcgangtcga                                                                    10

<210> SEQ ID NO 91
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: where n is dSpacer (a basic residue)
<220> FEATURE:
<221> NAME/KEY: misc_feature
<222> LOCATION: (10)..(10)
<223> OTHER INFORMATION: cholesterol

<400> SEQUENCE: 91 tcgacgtcna                                                                    10

<210> SEQ ID NO 92
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: where n is dSpacer (a basic residue)
<220> FEATURE:
<221> NAME/KEY: misc_feature
<222> LOCATION: (10)..(10)
<223> OTHER INFORMATION: cholesterol

<400> SEQUENCE: 92 tcganntcga                                                                    10

<210> SEQ ID NO 93
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where t is 5-Methoxythymidine
<220> FEATURE:
<221> NAME/KEY: misc_feature
<222> LOCATION: (10)..(10)
<223> OTHER INFORMATION: cholesterol
```

<400> SEQUENCE: 93
tcgacgtcga                                                                 10

<210> SEQ ID NO 94
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where t is 2'3'- Dideoxythymidine
<220> FEATURE:
<221> NAME/KEY: misc_feature
<222> LOCATION: (10)..(10)
<223> OTHER INFORMATION: cholesterol

<400> SEQUENCE: 94
tcgacgtcga                                                                 10

<210> SEQ ID NO 95
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where c is Ara-cytidine (5'5'- linked)
<220> FEATURE:
<221> NAME/KEY: misc_feature
<222> LOCATION: (10)..(10)
<223> OTHER INFORMATION: cholesterol

<400> SEQUENCE: 95
tcgacgtcga                                                                 10

<210> SEQ ID NO 96
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where c is 2'- Fluoro-cytidine
<220> FEATURE:
<221> NAME/KEY: misc_feature
<222> LOCATION: (10)..(10)
<223> OTHER INFORMATION: cholesterol

<400> SEQUENCE: 96
tcgacgtcga                                                                 10

<210> SEQ ID NO 97
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 2'- Fluoro-uridine
<220> FEATURE:
<221> NAME/KEY: misc_feature
<222> LOCATION: (10)..(10)

```
<223> OTHER INFORMATION: cholesterol

<400> SEQUENCE: 97 ncgacgncga                                                               10

<210> SEQ ID NO 98
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 2'-O-Methyl Uridine
<220> FEATURE:
<221> NAME/KEY: misc_feature
<222> LOCATION: (10)..(10)
<223> OTHER INFORMATION: cholesterol

<400> SEQUENCE: 98 ncgacgtcga                                                               10

<210> SEQ ID NO 99
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where all residues are 2'- or 3'-O-Methyl
      Ribonucleotides (A, C, G)
<220> FEATURE:
<221> NAME/KEY: misc_feature
<222> LOCATION: (1)..(10)
<223> OTHER INFORMATION: where n is 2'-O-Methyl Uridine
<220> FEATURE:
<221> NAME/KEY: misc_feature
<222> LOCATION: (10)..(10)
<223> OTHER INFORMATION: cholesterol

<400> SEQUENCE: 99 ncgacgncga                                                               10

<210> SEQ ID NO 100
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where n is Ribo-uridine
<220> FEATURE:
<221> NAME/KEY: misc_feature
<222> LOCATION: (10)..(10)
<223> OTHER INFORMATION: cholesterol

<400> SEQUENCE: 100 ncgacgtcga                                                               10

<210> SEQ ID NO 101
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: misc_feature
<222> LOCATION: (1)..(10)
<223> OTHER INFORMATION: where n is Ribo-uridine
<220> FEATURE:
<221> NAME/KEY: misc_feature
<222> LOCATION: (1)..(10)
<223> OTHER INFORMATION: where c, g, and a are ribonucleotides
<220> FEATURE:
<221> NAME/KEY: misc_feature
<222> LOCATION: (10)..(10)
<223> OTHER INFORMATION: cholesterol

<400> SEQUENCE: 101 ncgacgncga                                                                10

<210> SEQ ID NO 102
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where n is 2'-O-Methyl Uridine
<220> FEATURE:
<221> NAME/KEY: misc_feature
<222> LOCATION: (1)..(10)
<223> OTHER INFORMATION: where c, g, and a are 3'-O-Methyl-A (C, G)
<220> FEATURE:
<221> NAME/KEY: misc_feature
<222> LOCATION: (10)..(10)
<223> OTHER INFORMATION: cholesterol

<400> SEQUENCE: 102 ncgacgncga                                                                10

<210> SEQ ID NO 103
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: n is a, c, g, or t
<220> FEATURE:
<221> NAME/KEY: misc_feature
<222> LOCATION: (24)..(24)
<223> OTHER INFORMATION: cholesterol

<400> SEQUENCE: 103
tcgacgtcga nnnntcgacg tcga                                                24

<210> SEQ ID NO 104
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Spacer 9 (triethylenglycol phosphate)
<220> FEATURE:
<221> NAME/KEY: misc_feature
<222> LOCATION: (10)..(11)
<223> OTHER INFORMATION: 5'5' link
<220> FEATURE:
<221> NAME/KEY: misc_feature
<222> LOCATION: (12)..(14)
<223> OTHER INFORMATION: n is a, c, g, or t
```

```
<220> FEATURE:
<221> NAME/KEY: misc_feature
<222> LOCATION: (24)..(24)
<223> OTHER INFORMATION: cholesterol

<400> SEQUENCE: 104
agctgcagct nnnntcgacg tcga                                              24

<210> SEQ ID NO 105
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 105
tcaacgttga                                                              10

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: where the linkage is a phosphorothioate linkage
<220> FEATURE:
<221> NAME/KEY: misc_feature
<222> LOCATION: (3)..(5)
<223> OTHER INFORMATION: where the linkages are phosphorothioate
      linkages
<220> FEATURE:
<221> NAME/KEY: misc_feature
<222> LOCATION: (6)..(10)
<223> OTHER INFORMATION: where the linkages are phosphorothioate
      linkages
<220> FEATURE:
<221> NAME/KEY: misc_feature
<222> LOCATION: (11)..(13)
<223> OTHER INFORMATION: where the linkages are phosphorothioate
      linkages
<220> FEATURE:
<221> NAME/KEY: misc_feature
<222> LOCATION: (14)..(16)
<223> OTHER INFORMATION: where the linkages are phosphorothioate
      linkages
<220> FEATURE:
<221> NAME/KEY: misc_feature
<222> LOCATION: (16)..(16)
<223> OTHER INFORMATION: cholesterol

<400> SEQUENCE: 106
tcgtcgtttc gtcgtt                                                       16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (16)..(16)
<223> OTHER INFORMATION: cholesterol

<400> SEQUENCE: 107
```

```
tcgtcgtttc gtcgtt                                                       16
```

```
<210> SEQ ID NO 108
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: cholesterol

<400> SEQUENCE: 108
tcgtcgtcga                                                              10

<210> SEQ ID NO 109
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: cholesterol

<400> SEQUENCE: 109
tcgacgacga                                                              10

<210> SEQ ID NO 110
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: where the linkages are phosphorothioate
      linkages

<400> SEQUENCE: 110
acgacgtcgt                                                              10

<210> SEQ ID NO 111
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 111
tcgacgtcgt                                                              10

<210> SEQ ID NO 112
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 112
tcgacgtcga                                                              10

<210> SEQ ID NO 113
<211> LENGTH: 14
<212> TYPE: DNA
```

```
<213> ORGANISM: Artificial sequence
<220> FEATURE:
<223> OTHER INFORMATION: Synthetic oligonucleotide

<400> SEQUENCE: 113
cgacgtcgac gtcg                                                     14

<210> SEQ ID NO 114
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 114
cggcggccgc cg                                                       12

<210> SEQ ID NO 115
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 115
gacgatcgtc                                                          10

<210> SEQ ID NO 116
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 116
tcgtcgtttt gtcgttttgt cgtt                                          24
```